US007037695B2

(12) United States Patent
Hiebsch

(10) Patent No.: US 7,037,695 B2
(45) Date of Patent: May 2, 2006

(54) METHODS OF ASSESSING WOLFRAMIN PROTEIN ACTIVITY

(75) Inventor: Ronald R. Hiebsch, Kalamazoo, MI (US)

(73) Assignee: Pharmacia & Upjohn, Kalamazoo, MI (US)

( * ) Notice: Subject to any disclaimer, the term of this patent is extended or adjusted under 35 U.S.C. 154(b) by 397 days.

(21) Appl. No.: 10/060,425

(22) Filed: Jan. 30, 2002

(65) Prior Publication Data

US 2002/0164650 A1   Nov. 7, 2002

Related U.S. Application Data

(60) Provisional application No. 60/266,385, filed on Feb. 2, 2001.

(51) Int. Cl.
*C12N 9/00* (2006.01)
*C12N 15/00* (2006.01)
*C12N 1/20* (2006.01)
*C12Q 1/00* (2006.01)
*C07H 21/04* (2006.01)

(52) U.S. Cl. .......................... 435/183; 435/212; 435/4; 435/69.1; 435/252.3; 435/320.1; 536/23.2; 536/23.5

(58) Field of Classification Search ................ 435/212, 435/252.3, 320.1, 440, 24, 4, 18, 183, 69.1; 536/350, 23.2, 23.5; 514/789; 530/350
See application file for complete search history.

(56) References Cited

U.S. PATENT DOCUMENTS

| 5,776,689 | A | 7/1998 | Karin et al. ..................... 435/6 |
| 6,127,521 | A | 10/2000 | Berlin et al. ................. 530/350 |
| 6,248,527 | B1 | 6/2001 | Chen et al. ..................... 435/6 |
| 6,251,676 | B1 | 6/2001 | Shioda et al. ................. 435/455 |
| 6,316,223 | B1 | 11/2001 | Payan et al. ................. 435/69.1 |

FOREIGN PATENT DOCUMENTS

WO   WO 00/23784   4/2000

OTHER PUBLICATIONS

Bartel, P., et al., "Elimination of false positives that arise in using the two-hybrid system," Biotechniques 14(6):920-4 [1993].
Che, F-Y, et al., "Identification of peptides from brain and pituitary of $Cpe^{fat}$ / $Cpe^{fat}$ mice," PNAS 98(17):9971-76 [2001].
Chien, C-T, et al., "The two-hybrid system: A method to identify and clone genes for proteins that interact with a protein of interest," PNAS 88(21):9578-82 [1991].
Cool, D.R., et al., "Carboxypeptidase E is a regulated secretory pathway sorting receptor: Genetic obliteration leads to endocrine disorders in $Cpe^{fat}$ mice," Cell 88:73-83 [1997].
Dang, C.V. et al., "Intracellular leucine zipper interactions suggest c-Myc hetero-oligomerization," Molecular and Cellular Biology 11(2):954-62 [1991].
Dove, S.L. et al., "Conversion of the ω subunit of Escherichia coli RNA polymerase into a transcriptional activator or an activation target," Genes & Development 12:745-54 [1998].
Dove, S.L. et al., "Activation of prokaryotic transcription through arbitrary protein-protein contacts," Nature 386 (6625):627-30 [1997].
Duman, R.S. et al., "Neural Plasticity to stress and antidepressant treatment," Society of Biological Psychiatry 46:1181-91 [1999].
Durfee, T., et al., "The retinoblastoma protein associates with the protein phosphatase type 1 catalytic subunit," Genes & Development 7:555-69 [1993].
Fields, S. et al., "A novel genetic system to detect protein-protein interactions," Nature 340(6230):245-46 [1989].
Fricker, L.D., "Activation and membrane binding of carboxypeptidase E," J. Cellular Biochemistry 38:279-289 [1988].
Fricker, L.D. et al., "Purification and characterization of enkephalin convertase, an ankephalin-synthesizing carboxypeptidase," J. Biological Chemistry 258(18):10,950-955 [1983].
Fricker, L.D. et al., "Methods for studying carboxypeptidase E," Methods in Neurosciences 23:237-50 [1995].
Fricker, L.D.,"Peptide Biosynthesis and Processing: Chapter 8—Peptide processing exopeptidases: Amino-and Carboxypeptidases involved with peptide biosynthesis," pp. 199-230 CRC Press, Boca Raton, FL) [1991].
Gabreels, B.A.Th.F, et al., "The vasopressin precursor is not processed in the hypothalamus of Wolfram Syndrome patients with diabetes insipidus: Evidence for the involvement of PC2 and 7B2," J. Clinical Endocrinology & Metabolism 83(11):4026-33 [1998].
Hannon, G.J. et al., "Isolation of the Rb-related p130 through its interaction with CDK2 and cyclins," Genes & Development 7:2378-91 [1993].
Hardy, C.F.J. et al., "A RAP1-interacting protein involved in transcriptional silencing and telomere length regulation," Genes & Development 6:801-14 [1992].
Harper, J.W. et al., "The p21 Cdk-interacting protein Cip1 is a potent inhibitor of G1 cyclin-dependent kinases," Cell 75:805-16 [1993].

(Continued)

Primary Examiner—Manjunath Rao
Assistant Examiner—Yong Pak
(74) Attorney, Agent, or Firm—Edward F. Rehberg; Austin W. Zhang; Charles W. Ashbrook

(57) ABSTRACT

The present invention relates to a method of assaying modulators of the interaction between Wolframin protein and its identified cellular binding partner.

4 Claims, No Drawings

OTHER PUBLICATIONS

Inoue, H. et al., "A gene encoding a transmembrane protein is mutated in patients with diabetes mellitus and optic atrophy (Wolfram syndrome)," Nature Genetics 20:143-48 [1998].

Kadonaga, J.T. et al., "Affinity purification of sequence-specific DNA binding proteins," PNAS 83(16):5889-93 [1986].

Kohler, G. et al., "Continuous cultures of fused cells secreting antibody of predefined specificity," Nature 256(5517): 495-97 [1975].

LeDouarin, B., et al., "A new version of the two-hybrid assay for detection of protein-protein interactions," Nucleic Acids Research 23(5):876-78 [1995].

Luban, J. et al., "Human Immunodeficiency Virus type 1 Gag protein binds to cyclophilins A and B," Cell 73(6): 1067-78 [1993].

Manser, E. et al., "Human carboxypeptidase E," Biochem. J. 267(2):517-25 [1990].

Owen, M.J., "Psychiatric disorders in Wolfram syndrome heterozygotes," Molecular Psychiatry 3:12-13 [1998].

Parodi, L.A., et al., "A consensus procedure for predicting the location of α-Helical transmembrane segments in proteins," 10(5):527-35 [1994].

Silver, S.C. et al., "Techniques for cloning cDNAs encoding interactive transcriptional regulatory proteins," Molecular Biology Reports 17(3):155-65 [1993].

Song, L., et al., "The pro region is not required for the expression or intracellular routeing of carboxypeptidase E," Biochem. J. 323:265-71 [1997].

Sonnhammer, E.L.L. et al., "A hidden Markov model for predicting transmembrane helices in protein sequences," Proc. Int. Conf. Intell. Syst. Mol. Biol. 6:175-82 [1998].

Strom, T.M. et al., "Diabetes insipidus, diabetes mellitus, optic atrophy and deafness (DIDMOAD) caused by mutations in a novel gene (*wolframin*) coding for a predicted transmembrane protein," Human Molecular Genetics 7(13): 2021-28 [1998].

Swift, R.G., et al., "Psychiatric disorders in 36 families with Wolfram syndrome," Am. J. Psychiatry 148(6):775-79 [1991].

Swift, R.G. et al., "Predisposition of Wolfram syndrome heterozygotes to psychiatric illness," Molecular Psychiatry 3:86-91 [1998].

Torres, R. et al., "Mutation screening of the Wolfram syndrome gene in psychiatric patients," Molecular Psychiatry 6:39-43 [2001].

Varlamov, O. et al., "Induced and spontaneous mutations at $Ser^{202}$ of carboxypeptidase E," J. Biological Chemistry 271(24):13,981-986 [1996].

Vojtek, A.B. et al., "Mammalian Ras interacts directly with the serine/threonine kinase Raf," Cell:74(1):205-14 [1993].

Yang, X. et al., "A protein kinase substrate identified by the two-hybrid system," Science 257(5070):680-82 [1992].

Young, K. et al., "Identification of a calcium channel modulator using a high throughput yeast two-hybrid screen," Nature Biotechnology 16:946-50 [1998].

Zervos, A.S. et al., "Mxi1, a protein that specifically interacts with Max to bind Myc-Max recognition sites," Cell 72(2):223-32 [1993].

Awata Takuya et. al., "Missense variations of the gene responsible for Wolfram syndrome (WFS1/wolframin) in Japanese: Possible contribution of the Arg456His mutation to type 1 diabetes as a nonautoimmune genetic basis." *Biochemical and Biophysical Research Communications.*, vol. 268, No. 2, Feb. 16, 2000, pp. 612-616.

Varlamov Oleg et. al., "The C-terminal region of carboxypeptidase E involved in membrane binding is distinct from the region involved with intracellular routing." *Journal of Biological Chemistry.*, vol. 271, No. 11, 1996, pp. 6077-6083.

SEQUENCE LISTING

<160> NUMBER OF SEQ ID NOS: 17

<210> SEQ ID NO 1
<211> LENGTH: 2673
<212> TYPE: DNA
<213> ORGANISM: Homo sapiens

<400> SEQUENCE: 1

```
atggactcca acactgctcc gctgggcccc tcctgcccac agccccgcc  agcaccgcag      60 ccccaggcgc gttcccgact caatgccaca gcctcgttgg agcaggagag gagcgaaagg     120
ccccgagcac ccggacccca ggctggccct ggccctggtg ttagagacgc agcggccccc     180
gctgaacccc aggcccagca taccaggagc cgggaaagag cagacggcac cgggcctaca     240
aagggagaca tggaaatccc ctttgaagaa gtcctggaga gggccaaggc cggggacccc     300
aagcacagac tgaggtgggg gaagcactac ctgcagttgg ccggcgacac ggatgaagaa     360
ctcaacagct gcaccgctgt ggactggctg gtcctcgccg cgaagcaggg ccgtcgcgag     420
gctgtgaagc tgcttcgccg gtgcttggcg gacagaagag gcatcacgtc cgagaacgaa     480
cgggaggtga ggcagctctc ctccgagacc gacctggaga gggccgtgcg caaggcagcc     540
ctggtcatgt actggaagct caaccccaag aagaagaagc aggtggccgt ggcggagctg     600
ctggagaatg tcggccaggt caacgagcac gatggagggg cgcagccagg ccccgtgccc     660
aagtccctgc agaagcagag gcggatgctg gagcgcctgg tcagcagcga gtccaagaac     720
tacatcgcgc tggatgactt tgtggagatc actaagaagt acgccaaggg cgtcatcccc     780
agcagcctgt tcctgcagga cgacgaagat gatgacgagc tggcggggaa gagccctgag     840
```

|  |  |
|---|---|
| gacctgccac tgcgtctgaa ggtggtcaag taccccctgc acgccatcat ggagatcaag | 900 |
| gagtacctga ttgacatggc ctccagggca ggcatgcact ggctgtccac catcatcccc | 960 |
| acgcaccaca tcaacgcgct catcttcttc ttcatcatca gcaacctcac catcgacttc | 1020 |
| ttcgccttct tcatcccgct ggtcatcttc tacctgtcct tcatctccat ggtgatctgc | 1080 |
| accctcaagg tgttccagga cagcaaggcc tgggagaact tccgcaccct caccgacctg | 1140 |
| ctgctgcgct tcgagcccaa cctggatgtg agcaggccg aggttaactt cggctggaac | 1200 |
| cacctggagc cctatgccca tttcctgctc tctgtcttct tcgtcatctt ctccttcccc | 1260 |
| atcgccagca aggactgcat cccctgctcg agctggctg tcatcaccgg ctttctttacc | 1320 |
| gtgaccagct acctgagcct gagcacccat gcagagccct acacgcacag ggccctggcc | 1380 |
| accgaggtca ccgccggcct gctatcgctg ctgccctcca tgcccttgaa ttggccctac | 1440 |
| ctgaaggtcc ttggccagac cttcatcacc gtgcctgtcg gccacctggt cgtcctcaat | 1500 |
| gtcagcgtcc cgtgcctgct ctatgtctac ctgctctatc tcttcttccg catggcacag | 1560 |
| ctgaggaatt tcaagggcac ctactgctac cttgtgccct acctggtgtg cttcatgtgg | 1620 |
| tgtgagctct ccgtggtcat cctgctggag tccaccggcc tggggctgct ccgcgcctcc | 1680 |
| atcggctact tcctcttcct ctttgccctc cccatcctgg tggccggcct ggccctggtg | 1740 |
| ggcgtgctgc agttcgcccg gtggttcacg tctctggagc tcaccaagat cgcagtcacc | 1800 |
| gtggcggtct gtagtgtgcc cctgctgttg cgctggtgga ccaaggccag cttctctgtg | 1860 |
| gtggggatgg tgaagtccct gacgcggagc tccatggtca agctcatcct ggtgtggctc | 1920 |
| acggccatcg tgctgttctg ctggttctat gtgtaccgct cagagggcat gaaggtctac | 1980 |
| aactccacac tgacctggca gcagtatggt gcgctgtgcg ggccacgcgc ctggaaggag | 2040 |
| accaacatgg cgcgcaccca gatcctctgc agccactgg agggccacag ggtcacgtgg | 2100 |
| accgccgct tcaagtacgt ccgcgtgact gacatcgaca cagcgccga gtctgccatc | 2160 |
| aacatgctcc cgttcttcat cggcgactgg atgcgctgcc tctacggcga ggcctaccct | 2220 |
| gcctgcagcc ctggcaacac ctccacggcc gaggaggagc tctgtcgcct taagctgctg | 2280 |
| gccaagcacc cctgccacat caagaagttc gaccgctaca gtttgagat taccgtgggc | 2340 |
| atgccattca gcagcggcgc tgacggctcg cgcagccgcg aggaggacga cgtcaccaag | 2400 |
| gacatcgtgc tgcgggccag cagcgagttc aaaagcgtgc tgctcagcct cgcgcagggc | 2460 |
| agcctcatcg agttcagcac catcctggag ggccgcctgg cagcaagtg gcctgtcttc | 2520 |
| gagctcaagg ccatcagctg cctcaactgc atggcccagc tctcgcccac caggcggcac | 2580 |
| gtgaagatcg agcacgactg gcgcagcacc gtgcatggcg ccgtgaagtt cgccttcgac | 2640 |
| ttcttttttct tcccattcct gtcggcggcc tga | 2673 |

<210> SEQ ID NO 2
<211> LENGTH: 890
<212> TYPE: PRT
<213> ORGANISM: Homo sapiens

<400> SEQUENCE: 2

Met Asp Ser Asn Thr Ala Pro Leu Gly Pro Ser Cys Pro Gln Pro Pro
1               5                   10                  15

Pro Ala Pro Gln Pro Gln Ala Arg Ser Arg Leu Asn Ala Thr Ala Ser
            20                  25                  30

Leu Glu Gln Glu Arg Ser Glu Arg Pro Arg Ala Pro Gly Pro Gln Ala
        35                  40                  45

-continued

Gly Pro Gly Pro Gly Val Arg Asp Ala Ala Pro Ala Glu Pro Gln
             50                  55                  60

Ala Gln His Thr Arg Ser Arg Glu Arg Ala Asp Gly Thr Gly Pro Thr
65                      70                  75                  80

Lys Gly Asp Met Glu Ile Pro Phe Glu Glu Val Leu Glu Arg Ala Lys
                     85                  90                  95

Ala Gly Asp Pro Lys Ala Gln Thr Glu Val Gly Lys His Tyr Leu Gln
                100                 105                 110

Leu Ala Gly Asp Thr Asp Glu Glu Leu Asn Ser Cys Thr Ala Val Asp
             115                 120                 125

Trp Leu Val Leu Ala Ala Lys Gln Gly Arg Arg Glu Ala Val Lys Leu
130                 135                 140

Leu Arg Arg Cys Leu Ala Asp Arg Arg Gly Ile Thr Ser Glu Asn Glu
145                 150                 155                 160

Arg Glu Val Arg Gln Leu Ser Ser Glu Thr Asp Leu Glu Arg Ala Val
                165                 170                 175

Arg Lys Ala Ala Leu Val Met Tyr Trp Lys Leu Asn Pro Lys Lys Lys
                180                 185                 190

Lys Gln Val Ala Val Ala Glu Leu Leu Glu Asn Val Gly Gln Val Asn
                195                 200                 205

Glu His Asp Gly Gly Ala Gln Pro Gly Val Pro Lys Ser Leu Gln
210                 215                 220

Lys Gln Arg Arg Met Leu Glu Arg Leu Val Ser Ser Glu Ser Lys Asn
225                 230                 235                 240

Tyr Ile Ala Leu Asp Asp Phe Val Glu Ile Thr Lys Lys Tyr Ala Lys
                    245                 250                 255

Gly Val Ile Pro Ser Ser Leu Phe Leu Gln Asp Asp Glu Asp Asp Asp
                260                 265                 270

Glu Leu Ala Gly Lys Ser Pro Glu Asp Leu Pro Leu Arg Leu Lys Val
             275                 280                 285

Val Lys Tyr Pro Leu His Ala Ile Met Glu Ile Lys Glu Tyr Leu Ile
             290                 295                 300

Asp Met Ala Ser Arg Ala Gly Met His Trp Leu Ser Thr Ile Ile Pro
305                 310                 315                 320

Thr His His Ile Asn Ala Leu Ile Phe Phe Phe Ile Ile Ser Asn Leu
                325                 330                 335

Thr Ile Asp Phe Phe Ala Phe Phe Ile Pro Leu Val Ile Phe Tyr Leu
                340                 345                 350

Ser Phe Ile Ser Met Val Ile Cys Thr Leu Lys Val Phe Gln Asp Ser
             355                 360                 365

Lys Ala Trp Glu Asn Phe Arg Thr Leu Thr Asp Leu Leu Leu Arg Phe
             370                 375                 380

Glu Pro Asn Leu Asp Val Glu Gln Ala Glu Val Asn Phe Gly Trp Asn
385                 390                 395                 400

His Leu Glu Pro Tyr Ala His Phe Leu Leu Ser Val Phe Phe Val Ile
                405                 410                 415

Phe Ser Phe Pro Ile Ala Ser Lys Asp Cys Ile Pro Cys Ser Glu Leu
             420                 425                 430

Ala Val Ile Thr Gly Phe Phe Thr Val Thr Ser Tyr Leu Ser Leu Ser
             435                 440                 445

Thr His Ala Glu Pro Tyr Thr His Arg Ala Leu Ala Thr Glu Val Thr
450                 455                 460

```
Ala Gly Leu Leu Ser Leu Leu Pro Ser Met Pro Leu Asn Trp Pro Tyr
465                 470                 475                 480

Leu Lys Val Leu Gly Gln Thr Phe Ile Thr Val Pro Val Gly His Leu
                485                 490                 495

Val Val Leu Asn Val Ser Val Pro Cys Leu Leu Tyr Val Tyr Leu Leu
            500                 505                 510

Tyr Leu Phe Phe Arg Met Ala Gln Leu Arg Asn Phe Lys Gly Thr Tyr
        515                 520                 525

Cys Tyr Leu Val Pro Tyr Leu Val Cys Phe Met Trp Cys Glu Leu Ser
    530                 535                 540

Val Val Ile Leu Leu Glu Ser Thr Gly Leu Gly Leu Leu Arg Ala Ser
545                 550                 555                 560

Ile Gly Tyr Phe Leu Phe Leu Phe Ala Leu Pro Ile Leu Val Ala Gly
                565                 570                 575

Leu Ala Leu Val Gly Val Leu Gln Phe Ala Arg Trp Phe Thr Ser Leu
            580                 585                 590

Glu Leu Thr Lys Ile Ala Val Thr Val Ala Val Cys Ser Val Pro Leu
        595                 600                 605

Leu Leu Arg Trp Trp Thr Lys Ala Ser Phe Ser Val Val Gly Met Val
    610                 615                 620

Lys Ser Leu Thr Arg Ser Ser Met Val Lys Leu Ile Leu Val Trp Leu
625                 630                 635                 640

Thr Ala Ile Val Leu Phe Cys Trp Phe Tyr Val Tyr Arg Ser Glu Gly
                645                 650                 655

Met Lys Val Tyr Asn Ser Thr Leu Thr Trp Gln Gln Tyr Gly Ala Leu
            660                 665                 670

Cys Gly Pro Arg Ala Trp Lys Glu Thr Asn Met Ala Arg Thr Gln Ile
        675                 680                 685

Leu Cys Ser His Leu Glu Gly His Arg Val Thr Trp Thr Gly Arg Phe
    690                 695                 700

Lys Tyr Val Arg Val Thr Asp Ile Asp Asn Ser Ala Glu Ser Ala Ile
705                 710                 715                 720

Asn Met Leu Pro Phe Phe Ile Gly Asp Trp Met Arg Cys Leu Tyr Gly
                725                 730                 735

Glu Ala Tyr Pro Ala Cys Ser Pro Gly Asn Thr Ser Thr Ala Glu Glu
            740                 745                 750

Glu Leu Cys Arg Leu Lys Leu Leu Ala Lys His Pro Cys His Ile Lys
        755                 760                 765

Lys Phe Asp Arg Tyr Lys Phe Glu Ile Thr Val Gly Met Pro Phe Ser
    770                 775                 780

Ser Gly Ala Asp Gly Ser Arg Ser Arg Glu Glu Asp Asp Val Thr Lys
785                 790                 795                 800

Asp Ile Val Leu Arg Ala Ser Ser Glu Phe Lys Ser Val Leu Leu Ser
                805                 810                 815

Leu Arg Gln Gly Ser Leu Ile Glu Phe Ser Thr Ile Leu Glu Gly Arg
            820                 825                 830

Leu Gly Ser Lys Trp Pro Val Phe Glu Leu Lys Ala Ile Ser Cys Leu
        835                 840                 845

Asn Cys Met Ala Gln Leu Ser Pro Thr Arg Arg His Val Lys Ile Glu
    850                 855                 860
```

```
His Asp Trp Arg Ser Thr Val His Gly Ala Val Lys Phe Ala Phe Asp
865                 870                 875                 880

Phe Phe Phe Phe Pro Phe Leu Ser Ala Ala
            885                 890
```

<210> SEQ ID NO 3
<211> LENGTH: 1431
<212> TYPE: DNA
<213> ORGANISM: Homo sapiens

<400> SEQUENCE: 3

| | | | | | |
|---|---|---|---|---|---|
| atggccgggc | gagggggcag | cgcgctgctg | gctctgtgcg | gggcactggc | tgcctgcggg | 60 |
| tggctcctgg | gcgccgaagc | ccaggagccc | ggggcgcccg | cggcgggcat | gaggcggcgc | 120 |
| cggcggctgc | agcaagagga | cggcatctcc | ttcgagtacc | accgctaccc | cgagctgcgc | 180 |
| gaggcgctcg | tgtccgtgtg | gctgcagtgc | accgccatca | gcaggattta | cacggtgggg | 240 |
| cgcagcttcg | agggccggga | gctcctggtc | atcgagctgt | ccgacaaccc | tggcgtccat | 300 |
| gagcctggtg | agcctgaatt | taaatacatt | gggaatatgc | atgggaatga | ggctgttgga | 360 |
| cgagaactgc | tcattttctt | ggcccagtac | ctatgcaacg | aataccagaa | ggggaacgag | 420 |
| acaattgtca | acctgatcca | cagtacccgc | attcacatca | tgccttccct | gaacccagat | 480 |
| ggctttgaga | aggcagcgtc | tcagcctggt | gaactcaagg | actggtttgt | gggtcgaagc | 540 |
| aatgcccagg | gaatagatct | gaaccggaac | tttccagacc | tggataggat | agtgtacgtg | 600 |
| aatgagaaag | aaggtggtcc | aaataatcat | ctgttgaaaa | atatgaagaa | aattgtggat | 660 |
| caaaacacaa | agcttgctcc | tgagaccaag | gctgtcattc | attggattat | ggatattcct | 720 |
| tttgtgcttt | ctgccaatct | ccatggagga | gaccttgtgg | ccaattatcc | atatgatgag | 780 |
| acgcggagtg | gtagtgctca | cgaatacagc | tcctccccag | atgacgccat | tttccaaagc | 840 |
| ttggcccggg | catactcttc | tttcaacccg | gccatgtctg | accccaatcg | gccaccatgt | 900 |
| cgcaagaatg | atgatgacag | cagctttgta | gatggaacca | ccaacggtgg | tgcttggtac | 960 |
| agcgtacctg | gagggatgca | agacttcaat | taccttagca | gcaactgttt | tgagatcacc | 1020 |
| gtggagctta | gctgtgagaa | gttcccacct | gaagagactc | tgaagaccta | ctgggaggat | 1080 |
| aacaaaaact | ccctcattag | ctaccttgag | cagatacacc | gaggagttaa | aggatttgtc | 1140 |
| cgagaccttc | aagtaaccc | aattgcgaat | gccaccatct | ccgtggaagg | aatagaccac | 1200 |
| gatgttacat | ccgcaaagga | tggtgattac | tggagattgc | ttatacctgg | aaactataaa | 1260 |
| cttacagcct | cagctccagg | ctatctggca | ataacaaaga | aagtggcagt | tccttacagc | 1320 |
| cctgctgctg | gggttgattt | tgaactggag | tcatttcctg | aaaggaaaga | agaggagaag | 1380 |
| gaagaattga | tggaatggtg | gaaaatgatg | tcagaaactt | taaattttta | a | 1431 |

<210> SEQ ID NO 4
<211> LENGTH: 476
<212> TYPE: PRT
<213> ORGANISM: Homo sapiens

<400> SEQUENCE: 4

```
Met Ala Gly Arg Gly Gly Ser Ala Leu Leu Ala Leu Cys Gly Ala Leu
1               5                   10                  15

Ala Ala Cys Gly Trp Leu Leu Gly Ala Glu Ala Gln Glu Pro Gly Ala
                20                  25                  30

Pro Ala Ala Gly Met Arg Arg Arg Arg Leu Gln Gln Glu Asp Gly
        35                  40                  45
```

```
Ile Ser Phe Glu Tyr His Arg Tyr Pro Glu Leu Arg Glu Ala Leu Val
 50                  55                  60

Ser Val Trp Leu Gln Cys Thr Ala Ile Ser Arg Ile Tyr Thr Val Gly
 65                  70                  75                  80

Arg Ser Phe Glu Gly Arg Glu Leu Leu Val Ile Glu Leu Ser Asp Asn
                 85                  90                  95

Pro Gly Val His Glu Pro Gly Glu Pro Glu Phe Lys Tyr Ile Gly Asn
                100                 105                 110

Met His Gly Asn Glu Ala Val Gly Arg Glu Leu Leu Ile Phe Leu Ala
            115                 120                 125

Gln Tyr Leu Cys Asn Glu Tyr Gln Lys Gly Asn Glu Thr Ile Val Asn
            130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Glu Leu Lys Asp Trp Phe
                165                 170                 175

Val Gly Arg Ser Asn Ala Gln Gly Ile Asp Leu Asn Arg Asn Phe Pro
                180                 185                 190

Asp Leu Asp Arg Ile Val Tyr Val Asn Glu Lys Glu Gly Gly Pro Asn
                195                 200                 205

Asn His Leu Leu Lys Asn Met Lys Lys Ile Val Asp Gln Asn Thr Lys
            210                 215                 220

Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
                245                 250                 255

Pro Tyr Asp Glu Thr Arg Ser Gly Ser Ala His Glu Tyr Ser Ser Ser
                260                 265                 270

Pro Asp Asp Ala Ile Phe Gln Ser Leu Ala Arg Ala Tyr Ser Ser Phe
                275                 280                 285

Asn Pro Ala Met Ser Asp Pro Asn Arg Pro Pro Cys Arg Lys Asn Asp
            290                 295                 300

Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
                325                 330                 335

Phe Glu Ile Thr Val Glu Leu Ser Cys Glu Lys Phe Pro Pro Glu Glu
                340                 345                 350

Thr Leu Lys Thr Tyr Trp Glu Asp Asn Lys Asn Ser Leu Ile Ser Tyr
            355                 360                 365

Leu Glu Gln Ile His Arg Gly Val Lys Gly Phe Val Arg Asp Leu Gln
            370                 375                 380

Gly Asn Pro Ile Ala Asn Ala Thr Ile Ser Val Glu Gly Ile Asp His
385                 390                 395                 400

Asp Val Thr Ser Ala Lys Asp Gly Asp Tyr Trp Arg Leu Leu Ile Pro
                405                 410                 415

Gly Asn Tyr Lys Leu Thr Ala Ser Ala Pro Gly Tyr Leu Ala Ile Thr
                420                 425                 430

Lys Lys Val Ala Val Pro Tyr Ser Pro Ala Ala Gly Val Asp Phe Glu
                435                 440                 445
```

```
Leu Glu Ser Phe Ser Glu Arg Lys Glu Glu Glu Lys Glu Glu Leu Met
    450                 455                 460

Glu Trp Trp Lys Met Met Ser Glu Thr Leu Asn Phe
465                 470                 475

<210> SEQ ID NO 5
<211> LENGTH: 29
<212> TYPE: DNA
<213> ORGANISM: synthetic sequence

<400> SEQUENCE: 5
gatcgaattc atggactcca acactgctc                                         29

<210> SEQ ID NO 6
<211> LENGTH: 30
<212> TYPE: DNA
<213> ORGANISM: synthetic sequence

<400> SEQUENCE: 6
gatcgcggcc gccatgtcaa tcaggtactc                                        30

<210> SEQ ID NO 7
<211> LENGTH: 2673
<212> TYPE: DNA
<213> ORGANISM: Rattus norvegicus

<400> SEQUENCE: 7
atgagctcag gcaccccacc tccgagcccc tctggcccac ctcctccacc cgcaccacag         60
ccccaggccc gggcccggct caatgccacc acctcactgg agcaggacaa gattgaaccg        120
cctcgtgctc ctagacctca gcctgactcc agtgctggac gaagtgctgg ggaagcaacc        180
acgccggagc ctcgggcccc tcacgccagc agccgagaag ggacagataa agctggtccc        240
atgaaggcag atgtggagat cccctttgaa gaaatcctgg agaaggccaa ggctggagac        300
cccaaagcac agacagaggt gggcaaacac tacctgcgac ttgccaatga tgcagatgaa        360
gagctcaaca gctgctcggc tgtggcctgg ctaatcctgg cggccaagca gggcaggcgg        420
gaggccgtga agctgctgag gcggtgccta gctgaccgga aaggcatcac ttctgagaat        480
gaggccgagg tgaagcagct atcctctgag accgacctgg aaagggcagt gcgcaaggct        540
gccctggtca tgtactggaa actcaacccc aagaaaaaga gcaggtggc tgtgtctgag         600 ctgctggaga tgtcgggca ggtcaacgaa caggatggag gggcgcagcc aggccccgtc         660
cccaagtccc tgcagaagca gaggcgcatg ctggagcgtc tagtgagcag tgaatccaag        720
aactacattg ctctggacga ttttgtggag ctcaccaaga agtatgccaa gggcatcatc        780
cccaacaacc tgttcctgca ggatgaggat gaagatgaag acgagctgtc agggaagagc        840
cccgaggacc tgccactacg ccagaaggtg gtgaagtacc ccttacacgc catcatggag        900
atcaaagagt acctgattga cgtggcctcc aaggcaggca tgcactggct ctccaccatc        960
gtgcccaccc atcacatcaa cgccctcatc ttcttcttca tcatcagcaa cctaaccatc       1020
gacttcttcg ccttcttcat cccctggtg tcttctacc tgtccttcgt gtccatggtc         1080
atctgcaccc tcaaagtgtt ccaggacagc aaggcctggg agaacttccg cactctcacc       1140
gacctgctgc tgcgcttcga gcccaaccta gatgtggagc aggcggaagt gaacttcggc       1200
tggaaccacc tggagcctta catccacttc ctgctgtcag tcgtcttcgt gatcttctcc       1260
ttcccgctgg ccagcaagga ctgcatcccg tgctccgagc tcgctgtcgt ctccgccttc       1320
ttcacggtga cgagctacat gagtctgagc agctccgccg agccctacac caggcgggcc       1380
```

```
ctggtcactg aggtggctgc tgggctgctg tcccttctgc ccaccatgcc cgtggactgg    1440
cccttcctga aagcactcgg ccagacgttc ttcaccgtgc ccatcggcca cttcatcatc    1500
ctcaacgtca gcctccctg cctgctctat gtctatctct tttacctctt cttccgcatg     1560
gcccagctga ggaacttcaa gggcacctac tgctacctgt gccctacct ggtgtgcttc     1620 atgtggtgtg aactgtccgt ggtcatcctg ctccagtcca ccggcctggg cttggtccgt    1680
gcctccatcg gctacttcct cttcctcttt gccctcccca tcctggtggc tggccttgcc    1740
ctcatgggca ccgtgcagtt tgcccgatgg ttcctgtcac tggacctcac caagatcatg    1800
gtcaccacag tgatctgcag cgtgcccctg cttttccgct ggtggaccaa ggccaacttt    1860
tcggtggtgg gaatggtcaa gtccctgact cggagctcca tagtgaagct cattctggtg    1920
tggctcacgc ccatcctgct cttttgctgg ttctacgtgt accggtcgga aggcatgaag    1980
gtctacaatt ccacactcac ctggcagcaa tatggcttcc tgtgtgggcc acgggcctgg    2040
aaggagacta acatggcccg gacccagatc ctgtgcagcc acctggaggg ccacagggtc    2100
acgtggacag gccgcttcaa gtatgtccga gtgaccgaga tcgacaacag cgccgagtcg    2160
gccatcaaca tgctcccgtt cttcctgggt gactggatgc gctgcctgta cggtgaggcc    2220
tacccatcct gtagctctgg taacacgtcc acggctgagg aggagctctg ccgtctcaag    2280
cagctggcca agcaccccctg ccacatcaag aagtttgacc gctacaagtt tgagatcaca    2340
gtgggcatgc ccttcggcac caacggcaac cgcggccacg aagaagacga catcaccaag    2400
gacatcgtcc tgcgagccag cagcgagttc aaggacgtgc tgctgaacct gcgtcagggc    2460
agcctcatag agttcagcac catcctcgag ggccgcctgg gtagcaagtg gcccgtcttc    2520
gagctcaagg ccatcagctg cctcaattgc atgacacagc tgtcccctgc ccggaggcac    2580
gtaaagatcg aacaggactg gcgtagcacg gtgcacggtg ccctcaagtt cgccttcgac    2640
ttcttcttct tcccattcct gtctgccgcc tga                                 2673
```

<210> SEQ ID NO 8
<211> LENGTH: 890
<212> TYPE: PRT
<213> ORGANISM: Rattus norvegicus

<400> SEQUENCE: 8

```
Met Ser Ser Gly Thr Pro Pro Ser Pro Ser Gly Pro Pro Pro Pro
 1               5                  10                  15

Pro Ala Pro Gln Pro Gln Ala Arg Ala Arg Leu Asn Ala Thr Thr Ser
                20                  25                  30

Leu Glu Gln Asp Lys Ile Glu Pro Pro Arg Ala Pro Arg Pro Gln Pro
            35                  40                  45

Asp Ser Ser Ala Gly Arg Ser Ala Gly Glu Ala Thr Thr Pro Glu Pro
        50                  55                  60

Arg Ala Pro His Ala Ser Ser Arg Glu Gly Thr Asp Lys Ala Gly Pro
    65                  70                  75                  80

Met Lys Ala Asp Val Glu Ile Pro Phe Glu Glu Ile Leu Glu Lys Ala
                85                  90                  95

Lys Ala Gly Asp Pro Lys Ala Gln Thr Glu Val Gly Lys His Tyr Leu
            100                 105                 110

Arg Leu Ala Asn Asp Ala Asp Glu Glu Leu Asn Ser Cys Ser Ala Val
        115                 120                 125

Ala Trp Leu Ile Leu Ala Ala Lys Gln Gly Arg Arg Glu Ala Val Lys
    130                 135                 140
```

-continued

```
Leu Leu Arg Arg Cys Leu Ala Asp Arg Lys Gly Ile Thr Ser Glu Asn
145                 150                 155                 160

Glu Ala Glu Val Lys Gln Leu Ser Ser Glu Thr Asp Leu Glu Arg Ala
            165                 170                 175

Val Arg Lys Ala Ala Leu Val Met Tyr Trp Lys Leu Asn Pro Lys Lys
        180                 185                 190

Lys Lys Gln Val Ala Val Ser Glu Leu Leu Glu Asn Val Gly Gln Val
            195                 200                 205

Asn Glu Gln Asp Gly Gly Ala Gln Pro Gly Pro Val Pro Lys Ser Leu
    210                 215                 220

Gln Lys Gln Arg Arg Met Leu Glu Arg Leu Val Ser Ser Glu Ser Lys
225                 230                 235                 240

Asn Tyr Ile Ala Leu Asp Asp Phe Val Glu Leu Thr Lys Lys Tyr Ala
                245                 250                 255

Lys Gly Ile Ile Pro Asn Asn Leu Phe Leu Gln Asp Glu Asp Glu Asp
            260                 265                 270

Glu Asp Glu Leu Ser Gly Lys Ser Pro Glu Asp Leu Pro Leu Arg Gln
        275                 280                 285

Lys Val Val Lys Tyr Pro Leu His Ala Ile Met Glu Ile Lys Glu Tyr
    290                 295                 300

Leu Ile Asp Val Ala Ser Lys Ala Gly Met His Trp Leu Ser Thr Ile
305                 310                 315                 320

Val Pro Thr His His Ile Asn Ala Leu Ile Phe Phe Ile Ile Ser
                325                 330                 335

Asn Leu Thr Ile Asp Phe Phe Ala Phe Phe Ile Pro Leu Val Val Phe
                340                 345                 350

Tyr Leu Ser Phe Val Ser Met Val Ile Cys Thr Leu Lys Val Phe Gln
        355                 360                 365

Asp Ser Lys Ala Trp Glu Asn Phe Arg Thr Leu Thr Asp Leu Leu Leu
    370                 375                 380

Arg Phe Glu Pro Asn Leu Asp Val Glu Gln Ala Glu Val Asn Phe Gly
385                 390                 395                 400

Trp Asn His Leu Glu Pro Tyr Ile His Phe Leu Leu Ser Val Val Phe
                405                 410                 415

Val Ile Phe Ser Phe Pro Leu Ala Ser Lys Asp Cys Ile Pro Cys Ser
            420                 425                 430

Glu Leu Ala Val Val Ser Ala Phe Phe Thr Val Thr Ser Tyr Met Ser
        435                 440                 445

Leu Ser Ser Ser Ala Glu Pro Tyr Thr Arg Arg Ala Leu Val Thr Glu
    450                 455                 460

Val Ala Ala Gly Leu Leu Ser Leu Leu Pro Thr Met Pro Val Asp Trp
465                 470                 475                 480

Pro Phe Leu Lys Ala Leu Gly Gln Thr Phe Phe Thr Val Pro Ile Gly
                485                 490                 495

His Phe Ile Ile Leu Asn Val Ser Leu Pro Cys Leu Leu Tyr Val Tyr
            500                 505                 510

Leu Phe Tyr Leu Phe Phe Arg Met Ala Gln Leu Arg Asn Phe Lys Gly
        515                 520                 525

Thr Tyr Cys Tyr Leu Val Pro Tyr Leu Val Cys Phe Met Trp Cys Glu
    530                 535                 540

Leu Ser Val Val Ile Leu Leu Gln Ser Thr Gly Leu Gly Leu Val Arg
545                 550                 555                 560
```

-continued

| | | | | | | | | | | | |
|---|---|---|---|---|---|---|---|---|---|---|---|
|Ala|Ser|Ile|Gly|Tyr|Phe|Leu|Phe|Leu|Phe|Ala|Leu|Pro|Ile|Leu|Val|
| | |565| | | |570| | | |575| |

Ala Gly Leu Ala Leu Met Gly Thr Val Gln Phe Ala Arg Trp Phe Leu
　　　　　　580　　　　　　　　585　　　　　　　　590

Ser Leu Asp Leu Thr Lys Ile Met Val Thr Thr Val Ile Cys Ser Val
　　　　595　　　　　　　　600　　　　　　　　605

Pro Leu Leu Phe Arg Trp Trp Thr Lys Ala Asn Phe Ser Val Val Gly
　　610　　　　　　　　615　　　　　　　　620

Met Val Lys Ser Leu Thr Arg Ser Ser Ile Val Lys Leu Ile Leu Val
625　　　　　　　　630　　　　　　　　635　　　　　　　　640

Trp Leu Thr Ala Ile Leu Leu Phe Cys Trp Phe Tyr Val Tyr Arg Ser
　　　　　　　　645　　　　　　　　650　　　　　　　　655

Glu Gly Met Lys Val Tyr Asn Ser Thr Leu Thr Trp Gln Gln Tyr Gly
　　　　　　660　　　　　　　　665　　　　　　　　670

Phe Leu Cys Gly Pro Arg Ala Trp Lys Glu Thr Asn Met Ala Arg Thr
　　　　675　　　　　　　　680　　　　　　　　685

Gln Ile Leu Cys Ser His Leu Glu Gly His Arg Val Thr Trp Thr Gly
　　690　　　　　　　　695　　　　　　　　700

Arg Phe Lys Tyr Val Arg Val Thr Glu Ile Asp Asn Ser Ala Glu Ser
705　　　　　　　　710　　　　　　　　715　　　　　　　　720

Ala Ile Asn Met Leu Pro Phe Phe Leu Gly Asp Trp Met Arg Cys Leu
　　　　　　　　725　　　　　　　　730　　　　　　　　735

Tyr Gly Glu Ala Tyr Pro Ser Cys Ser Ser Gly Asn Thr Ser Thr Ala
　　　　　　740　　　　　　　　745　　　　　　　　750

Glu Glu Glu Leu Cys Arg Leu Lys Gln Leu Ala Lys His Pro Cys His
　　　　755　　　　　　　　760　　　　　　　　765

Ile Lys Lys Phe Asp Arg Tyr Lys Phe Glu Ile Thr Val Gly Met Pro
　　770　　　　　　　　775　　　　　　　　780

Phe Gly Thr Asn Gly Asn Arg Gly His Glu Glu Asp Ile Thr Lys
785　　　　　　　　790　　　　　　　　795　　　　　　　　800

Asp Ile Val Leu Arg Ala Ser Ser Glu Phe Lys Asp Val Leu Leu Asn
　　　　　　　　805　　　　　　　　810　　　　　　　　815

Leu Arg Gln Gly Ser Leu Ile Glu Phe Ser Thr Ile Leu Glu Gly Arg
　　　　　　820　　　　　　　　825　　　　　　　　830

Leu Gly Ser Lys Trp Pro Val Phe Glu Leu Lys Ala Ile Ser Cys Leu
　　　　835　　　　　　　　840　　　　　　　　845

Asn Cys Met Thr Gln Leu Ser Pro Ala Arg Arg His Val Lys Ile Glu
　　850　　　　　　　　855　　　　　　　　860

Gln Asp Trp Arg Ser Thr Val His Gly Ala Leu Lys Phe Ala Phe Asp
865　　　　　　　　870　　　　　　　　875　　　　　　　　880

Phe Phe Phe Phe Pro Phe Leu Ser Ala Ala
　　　　　　　　885　　　　　　　　890

<210> SEQ ID NO 9
<211> LENGTH: 2673
<212> TYPE: DNA
<213> ORGANISM: Mus musculus

<400> SEQUENCE: 9

```
atgaactcag gcaccccacc tccgagcccc tctggcccac ctcctccacc cgcaccacag    60
ccccaggccc gggcccggct caatgccacc gcctcactgg agcaggacaa gattgaaccg   120
cctcgtgctc ccagacctca ggctgacccc agtgctggac gaagtgctgg ggaagcagcc   180
gctccggagc ctcgggcccc tcaaaccggc agccgggaag aaacggacag agctggtccc   240
```

-continued

```
atgaaggcag atgtggagat ccccttttgaa gaagtcctgg agaaagccaa ggctggagac    300
cccaaagcac agactgaggt gggcaaacac tacctacgcc ttgccaacga tgcagatgaa    360
gaactcaaca gctgctcagc cgtagcctgg ctaatcctgg cagccaagca gggcaggcgg    420
gaggccgtga agctgctgag gcggtgccta gctgaccgga aaggcatcac ttctgagaac    480
gaggctgagg tgaagcagct atcctctgag accgacctgg aaaggctgt gcgcaaggct    540 gccctggtca tgtactggaa actcaacccc aagaagaaga agcaggtggc tgtgtccgag    600
ctgctggaga tgttggaca gtcaacgag caggatggag gggcgcagcc aggcccagtc    660
cccaagtccc tgcagaagca gaggcgcatg ctggagcgcc tcgtcagcag tgaatccaag    720
aactacattg ctctggacga ttttgtggag ctcaccaaga agtacgccaa gggcatcatt    780
cccaccaacc tgttcctgca ggatgaggat gaagatgagg acgagctggc agggaagagc    840
cccgaggacc tgccactacg ccagaaggtg gtgaagtacc ctttacacgc catcatggag    900
atcaaagagt acctgattga cgtagcctcc aaggccggca tgcactggct ctccaccatt    960
gtacccaccc atcacatcaa cgccctcatc ttcttcttca tcatcagcaa cctaaccatc   1020
gacttcttcg ccttcttcat cccctggtg gtcttctatc tgtcctttgt gtccatggtc   1080
atctgcacgc tcaaggtgtt ccaggacagc aaggcctggg agaacttccg tactctcacc   1140
gacctgctgc tgcgcttcga gcccaaccta gacgtggagc aggccgaagt gaacttcggc   1200
tggaaccacc tggagcccta catccacttc ctactgtcag tcgtctttgt catcttctcc   1260
ttcccgctgg ccagcaagga ctgcatcccc tgctcggagc tggccgtcat ctccaccttc   1320
ttcacggtga ccagctacat gagcctgagc agctctgctg agccctatac caggcgtgcc   1380
ctggtcaccg aggtggctgc cggcttgctg tcccttctgc ccaccgtgcc tgtggactgg   1440
cgcttcctga agtactcgg ccagactttc ttcactgtgc ccgttggcca cttcatcatc   1500
ctcaacgtca gcctccctg cctgctctat gtctatctct tttacctctt cttccgcatg   1560
gcccagctga ggaacttcaa gggcacttat tgctacctgg tgccctacct ggtgtgcttc   1620
atgtggtgtg aactgtccgt ggtcatcctg ctccagtcta ccggcctggg cttggtccgg   1680
gcctccatcg gctacttcct cttcctcttt gccctcccca tcctggtggc tggcctcgcc   1740
ttgatgggca cggtgcagtt tgcccgatgg ttcctgtcgc tggacctcac caagatcatg   1800
gtcaccacgg tgatctgcgg cgtacccctg cttttccgtt ggtggaccaa ggccaacttc   1860
tcagtgatgg ggatggtcaa gtccctgacg aagagctcca tggtgaagct cattctggtg   1920
tggctaacgg ccatcctgct cttctgctgg ttctacgtgt accgctcaga aggcatgaag   1980
gtctacaact ccacactcac ctggcagcaa tatggcttcc tatgtgggcc ccgggcctgg   2040
aaggaaacta acatggcccg gacccagatc ctgtgcagcc acctggaggg ccacagggtc   2100
acgtggacag gccgcttcaa gtatgtccga gtgaccgaga tcgacaacag tgctgagtcg   2160
gccatcaaca tgctcccgtt cttcctgggc gattggatgc gctgcctgta tggcgaggcc   2220
tacccatctt gtagctctgg taacacgtcc acggcagagg aggagctctg ccgtctcaag   2280
cagctggcca agcacccctg ccacatcaag aagtttgacc gctacaaatt tgagatcaca   2340
gtgggcatgc cctttggcac caacggcaac cgcggccatg aagaggacga catcaccaag   2400
gacattgttc tccgtgccag cagcgagttc aaggacgtgt gctgaacct gcgccagggg   2460 agcctcatag agttcagcac catcctcgag ggccgcctgg gtagcaagtg gcccgtcttc   2520
gagctcaagg ccatcagctg cctcaactgc atgacgcagc tgtcacctgc ccggaggcac   2580
```

```
gtgaagatcg aacaggactg gcgtagcaca gtgcacggtg ccctcaagtt tgccttcgac    2640
ttcttcttct tcccattcct gtctgccgcc tga                                2673
```

<210> SEQ ID NO 10
<211> LENGTH: 890
<212> TYPE: PRT
<213> ORGANISM: Mus musculus

<400> SEQUENCE: 10

```
Met Asn Ser Gly Thr Pro Pro Ser Pro Ser Gly Pro Pro Pro
1               5                   10                  15

Pro Ala Pro Gln Pro Gln Ala Arg Ala Arg Leu Asn Ala Thr Ala Ser
                20                  25                  30

Leu Glu Gln Asp Lys Ile Glu Pro Pro Arg Ala Pro Arg Pro Gln Ala
            35                  40                  45

Asp Pro Ser Ala Gly Arg Ser Ala Gly Glu Ala Ala Pro Glu Pro
    50                  55                  60

Arg Ala Pro Gln Thr Gly Ser Arg Glu Glu Thr Asp Arg Ala Gly Pro
65                  70                  75                  80

Met Lys Ala Asp Val Glu Ile Pro Phe Glu Glu Val Leu Glu Lys Ala
                85                  90                  95

Lys Ala Gly Asp Pro Lys Ala Gln Thr Glu Val Gly Lys His Tyr Leu
            100                 105                 110

Arg Leu Ala Asn Asp Ala Asp Glu Glu Leu Asn Ser Cys Ser Ala Val
        115                 120                 125

Ala Trp Leu Ile Leu Ala Ala Lys Gln Gly Arg Arg Glu Ala Val Lys
    130                 135                 140

Leu Leu Arg Arg Cys Leu Ala Asp Arg Lys Gly Ile Thr Ser Glu Asn
145                 150                 155                 160

Glu Ala Glu Val Lys Gln Leu Ser Ser Glu Thr Asp Leu Glu Arg Ala
                165                 170                 175

Val Arg Lys Ala Ala Leu Val Met Tyr Trp Lys Leu Asn Pro Lys Lys
            180                 185                 190

Lys Lys Gln Val Ala Val Ser Glu Leu Leu Glu Asn Val Gly Gln Val
        195                 200                 205

Asn Glu Gln Asp Gly Gly Ala Gln Pro Gly Pro Val Pro Lys Ser Leu
    210                 215                 220

Gln Lys Gln Arg Arg Met Leu Glu Arg Leu Val Ser Ser Glu Ser Lys
225                 230                 235                 240

Asn Tyr Ile Ala Leu Asp Asp Phe Val Glu Leu Thr Lys Lys Tyr Ala
                245                 250                 255

Lys Gly Ile Ile Pro Thr Asn Leu Phe Leu Gln Asp Glu Asp Glu Asp
            260                 265                 270

Glu Asp Glu Leu Ala Gly Lys Ser Pro Glu Asp Leu Pro Leu Arg Gln
        275                 280                 285

Lys Val Val Lys Tyr Pro Leu His Ala Ile Met Glu Ile Lys Glu Tyr
    290                 295                 300

Leu Ile Asp Val Ala Ser Lys Ala Gly Met His Trp Leu Ser Thr Ile
305                 310                 315                 320

Val Pro Thr His His Ile Asn Ala Leu Ile Phe Phe Ile Ile Ser
                325                 330                 335

Asn Leu Thr Ile Asp Phe Phe Ala Phe Phe Ile Pro Leu Val Val Phe
            340                 345                 350
```

-continued

```
Tyr Leu Ser Phe Val Ser Met Val Ile Cys Thr Leu Lys Val Phe Gln
        355                 360                 365

Asp Ser Lys Ala Trp Glu Asn Phe Arg Thr Leu Thr Asp Leu Leu Leu
    370                 375                 380

Arg Phe Glu Pro Asn Leu Asp Val Glu Gln Ala Glu Val Asn Phe Gly
385                 390                 395                 400

Trp Asn His Leu Glu Pro Tyr Ile His Phe Leu Leu Ser Val Val Phe
                405                 410                 415

Val Ile Phe Ser Phe Pro Leu Ala Ser Lys Asp Cys Ile Pro Cys Ser
            420                 425                 430

Glu Leu Ala Val Ile Ser Thr Phe Thr Val Thr Ser Tyr Met Ser
        435                 440                 445

Leu Ser Ser Ala Glu Pro Tyr Thr Arg Arg Ala Leu Val Thr Glu
    450                 455                 460

Val Ala Ala Gly Leu Leu Ser Leu Leu Pro Thr Val Pro Val Asp Trp
465                 470                 475                 480

Arg Phe Leu Lys Val Leu Gly Gln Thr Phe Phe Thr Val Pro Val Gly
                485                 490                 495

His Phe Ile Ile Leu Asn Val Ser Leu Pro Cys Leu Leu Tyr Val Tyr
            500                 505                 510

Leu Phe Tyr Leu Phe Phe Arg Met Ala Gln Leu Arg Asn Phe Lys Gly
        515                 520                 525

Thr Tyr Cys Tyr Leu Val Pro Tyr Leu Val Cys Phe Met Trp Cys Glu
    530                 535                 540

Leu Ser Val Val Ile Leu Leu Gln Ser Thr Gly Leu Gly Leu Val Arg
545                 550                 555                 560

Ala Ser Ile Gly Tyr Phe Leu Phe Leu Phe Ala Leu Pro Ile Leu Val
                565                 570                 575

Ala Gly Leu Ala Leu Met Gly Thr Val Gln Phe Ala Arg Trp Phe Leu
            580                 585                 590

Ser Leu Asp Leu Thr Lys Ile Met Val Thr Thr Val Ile Cys Gly Val
        595                 600                 605

Pro Leu Leu Phe Arg Trp Trp Thr Lys Ala Asn Phe Ser Val Met Gly
    610                 615                 620

Met Val Lys Ser Leu Thr Lys Ser Ser Met Val Lys Leu Ile Leu Val
625                 630                 635                 640

Trp Leu Thr Ala Ile Leu Leu Phe Cys Trp Phe Tyr Val Tyr Arg Ser
                645                 650                 655

Glu Gly Met Lys Val Tyr Asn Ser Thr Leu Thr Trp Gln Gln Tyr Gly
            660                 665                 670

Phe Leu Cys Gly Pro Arg Ala Trp Lys Glu Thr Asn Met Ala Arg Thr
        675                 680                 685

Gln Ile Leu Cys Ser His Leu Glu Gly His Arg Val Thr Trp Thr Gly
    690                 695                 700

Arg Phe Lys Tyr Val Arg Val Thr Glu Ile Asp Asn Ser Ala Glu Ser
705                 710                 715                 720

Ala Ile Asn Met Leu Pro Phe Phe Leu Gly Asp Trp Met Arg Cys Leu
                725                 730                 735

Tyr Gly Glu Ala Tyr Pro Ser Cys Ser Ser Gly Asn Thr Ser Thr Ala
            740                 745                 750

Glu Glu Glu Leu Cys Arg Leu Lys Gln Leu Ala Lys His Pro Cys His
        755                 760                 765
```

```
Ile Lys Lys Phe Asp Arg Tyr Lys Phe Glu Ile Thr Val Gly Met Pro
        770                 775                 780
Phe Gly Thr Asn Gly Asn Arg Gly His Glu Glu Asp Asp Ile Thr Lys
785                 790                 795                 800
Asp Ile Val Leu Arg Ala Ser Ser Glu Phe Lys Asp Val Leu Leu Asn
                805                 810                 815
Leu Arg Gln Gly Ser Leu Ile Glu Phe Ser Thr Ile Leu Glu Gly Arg
            820                 825                 830
Leu Gly Ser Lys Trp Pro Val Phe Glu Leu Lys Ala Ile Ser Cys Leu
        835                 840                 845
Asn Cys Met Thr Gln Leu Ser Pro Ala Arg Arg His Val Lys Ile Glu
    850                 855                 860
Gln Asp Trp Arg Ser Thr Val His Gly Ala Leu Lys Phe Ala Phe Asp
865                 870                 875                 880
Phe Phe Phe Phe Pro Phe Leu Ser Ala Ala
                885                 890
```

<210> SEQ ID NO 11
<211> LENGTH: 1431
<212> TYPE: DNA
<213> ORGANISM: Rattus sp.

<400> SEQUENCE: 11

```
atggccgggc gcggaggacg ggtgctgctg gcgctgtgtg ccgcgctggt ggccggcggg      60
tggctgttag cggctgaagc ccaggagccc ggggcgccag cggctggcat gcggcggcgc     120
cggcggctgc agcaggagga cggcatctcc ttcgagtacc accgctatcc cgagctgcgc     180
gaggcgctgg tgtcggtatg gctgcagtgc accgccatca gcaggatcta cacggtgggg     240
cgcagcttcg agggccggga gctcctggtc atcgagctgt ctgacaaccc cggggtccat     300
gagcccggtg aacctgagtt taaatacatt gggaacatgc atggtaatga ggcggttgga     360
cgggagctgc tcattttctt ggcccagtac ctgtgtaacg aataccagag agggaatgag     420
acaattgtca acctgatcca gcacacacga atccatatca tgccctcctt gaaccccgat     480
ggctttgaga agcagcatc tcagcccggt gagctgaagg actggttcgt gggccgcagc     540
aatgcccagg gaatagatct gaaccggaac ttcccagact ggataggat cgtgtatgtt     600
aatgagaaag aaggcggtcc caacaaccac ctgctgaaga tctgaagaa aattgtggac     660
caaaattcaa agcttgcccc cgagaccaag gctgtcattc actggatcat ggacatccca     720
tttgtgctct ctgccaacct gcacggagga gacctcgtgg ctaattaccc gtatgatgag     780
acgcggagtg gtactgctca cgaatacagt tcctgccctg atgacgcaat tttccaaagc     840
ttggctcgcg catactcttc tttcaaccca gtcatgtctg accccaatcg acctccctgt     900
cgcaagaatg atgatgacag tagctttgta gatggaacaa ccaatggtgg tgcatggtac     960
agcgtccccg gtgaatgca agacttcaat tacctgagca gcaactgctt tgagatcact    1020
gtggagctta gctgtgagaa gttcccacct gaagagactc tcaaaagcta ctgggaagat    1080
aacaaaaact ccctcatcaa ctacctggag cagatacacc gaggtgttaa agggtttgtc    1140
cgtgaccttc aaggtaatcc gattgccaac gcaaccattt ccgtggatgg gatagaccat    1200
gatgtcacct cggctaagga tggggattac tggcgattgc ttgcgcctgg aaactataaa    1260
cttacagcct cagctcccgg ctacctggca atcacaaaga agtggcagt tcctttcagc    1320
cctgctgttg gggtggactt tgagctggag tctttctatg aaaggaagga ggaggagaag    1380
gaagaattga tggagtggtg gaaaatgatg tcagagactt tgaatttta a              1431
```

-continued

<210> SEQ ID NO 12
<211> LENGTH: 476
<212> TYPE: PRT
<213> ORGANISM: Rattus sp.

<400> SEQUENCE: 12

```
Met Ala Gly Arg Gly Arg Val Leu Leu Ala Leu Cys Ala Ala Leu
1               5                   10                  15

Val Ala Gly Gly Trp Leu Leu Ala Ala Glu Ala Gln Glu Pro Gly Ala
            20                  25                  30

Pro Ala Ala Gly Met Arg Arg Arg Arg Leu Gln Gln Glu Asp Gly
            35                  40                  45

Ile Ser Phe Glu Tyr His Arg Tyr Pro Glu Leu Arg Glu Ala Leu Val
    50                  55                  60

Ser Val Trp Leu Gln Cys Thr Ala Ile Ser Arg Ile Tyr Thr Val Gly
65                  70                  75                  80

Arg Ser Phe Glu Gly Arg Glu Leu Leu Val Ile Glu Leu Ser Asp Asn
                85                  90                  95

Pro Gly Val His Glu Pro Gly Glu Pro Glu Phe Lys Tyr Ile Gly Asn
                100                 105                 110

Met His Gly Asn Glu Ala Val Gly Arg Glu Leu Leu Ile Phe Leu Ala
            115                 120                 125

Gln Tyr Leu Cys Asn Glu Tyr Gln Arg Gly Asn Glu Thr Ile Val Asn
    130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Glu Leu Lys Asp Trp Phe
                165                 170                 175

Val Gly Arg Ser Asn Ala Gln Gly Ile Asp Leu Asn Arg Asn Phe Pro
                180                 185                 190

Asp Leu Asp Arg Ile Val Tyr Val Asn Glu Lys Glu Gly Gly Pro Asn
        195                 200                 205

Asn His Leu Leu Lys Asn Leu Lys Lys Ile Val Asp Gln Asn Ser Lys
    210                 215                 220

Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
                245                 250                 255

Pro Tyr Asp Glu Thr Arg Ser Gly Thr Ala His Glu Tyr Ser Ser Cys
                260                 265                 270

Pro Asp Asp Ala Ile Phe Gln Ser Leu Ala Arg Ala Tyr Ser Ser Phe
        275                 280                 285

Asn Pro Val Met Ser Asp Pro Asn Arg Pro Pro Cys Arg Lys Asn Asp
    290                 295                 300

Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
                325                 330                 335

Phe Glu Ile Thr Val Glu Leu Ser Cys Glu Lys Phe Pro Pro Glu Glu
                340                 345                 350

Thr Leu Lys Ser Tyr Trp Glu Asp Asn Lys Asn Ser Leu Ile Asn Tyr
        355                 360                 365

Leu Glu Gln Ile His Arg Gly Val Lys Gly Phe Val Arg Asp Leu Gln
    370                 375                 380
```

```
Gly Asn Pro Ile Ala Asn Ala Thr Ile Ser Val Asp Gly Ile Asp His
385                 390                 395                 400

Asp Val Thr Ser Ala Lys Asp Gly Asp Tyr Trp Arg Leu Leu Ala Pro
                405                 410                 415

Gly Asn Tyr Lys Leu Thr Ala Ser Ala Pro Gly Tyr Leu Ala Ile Thr
            420                 425                 430

Lys Lys Val Ala Val Pro Phe Ser Pro Ala Val Gly Val Asp Phe Glu
        435                 440                 445

Leu Glu Ser Phe Tyr Glu Arg Lys Glu Glu Lys Glu Glu Leu Met
    450                 455                 460

Glu Trp Trp Lys Met Met Ser Glu Thr Leu Asn Phe
465                 470                 475
```

<210> SEQ ID NO 13
<211> LENGTH: 1431
<212> TYPE: DNA
<213> ORGANISM: Murinae gen. sp.

<400> SEQUENCE: 13

```
atggccgggc gcggaggacg ggtgctgctg gcgctgtgtg ccgcgctggt ggccggcggg      60
tggctgctga cggctgaagc ccaggagccc ggggcgccag cggctggcat gaggcgccgc     120
cggcggctcc agcaagagga cggcatctcc ttcgagtacc accgctatcc agagctgcgc     180
gaggcgctgg tgtccgtatg gctgcagtgc accgccatca gcagaatcta cacagtgggg     240
cgcagcttcg agggccggga gctcctggtc atcgagctgt ctgacaaccc cggggtccat     300
gagccgggtg aacctgaatt taaatacatt gggaacatgc atggtaatga ggcggttgga     360
cgggaactgc ttatttctt ggcccagtac ctgtgtaacg agtaccagaa aggcaatgag     420
acaattgtca acctgatcca cagcacccga attcatatca tgccctcctt gaaccccgac     480
ggctttgaga agccgcatc gcagcccggc gagctgaagg actggtttgt gggccgcagc     540
aacgcccagg aatagatct gaaccgtaac ttcccagacc tggacaggat cgtgtatgtt     600
aatgagaaag aaggcggtcc taacaatcac ctgctgaaga tctgaagaa aattgtggac     660
caaaattcaa agcttgcccc cgagaccaag gctgtcattc actggatcat ggacattcca     720
tttgtgcttt ctgccaatct gcacggagga gaccttgtgg ctaattaccc atatgatgag     780
acacggagcg gtactgctca cgaatacagt tcctgccctg atgacgcaat tttccaaagc     840
ttggctcgcg cgtactcttc tttcaaccca gtcatgtctg accccaatcg acctccctgt     900
cgcaagaatg acgatgacag cagctttgta gatggaacga ccaatggtgg tgcatggtac     960
agcgtccccg gtgaatgca agacttcaat tacctgagca gcaactgctt cgagatcact    1020
gtggagctta gctgtgagaa gttcccaccg gaagagactc tcaaaagcta ctgggaagat    1080
aacaaaaact ccctcatcag ctacctggag cagatacacc gaggtgttaa agggtttgtc    1140
cgtgaccttc aggtaacccc gattgccaac gcaaccatct ctgtggacgg gatagaccat    1200
gatgtcacct cggctaagga tggggattac tggcgattgc ttgctcctgg aaactataaa    1260
cttacagcct ccgctcctgg ctacctggca atcacaaaga agtggcagt tccttttagc    1320
cctgctgttg gggtggactt tgagcttgag tctttctctg aaaggaagga ggaggagaag    1380
gaagaattga tggagtggtg gaaaatgatg tcagaaactt gaatttttta a             1431
```

<210> SEQ ID NO 14
<211> LENGTH: 476
<212> TYPE: PRT
<213> ORGANISM: Murinae gen. sp.

<400> SEQUENCE: 14

```
Met Ala Gly Arg Gly Arg Val Leu Leu Ala Leu Cys Ala Ala Leu
1               5                   10                  15

Val Ala Gly Gly Trp Leu Leu Thr Ala Glu Ala Gln Glu Pro Gly Ala
            20                  25                  30

Pro Ala Ala Gly Met Arg Arg Arg Arg Leu Gln Gln Glu Asp Gly
            35                  40                  45

Ile Ser Phe Glu Tyr His Arg Tyr Pro Glu Leu Arg Glu Ala Leu Val
50                  55                  60

Ser Val Trp Leu Gln Cys Thr Ala Ile Ser Arg Ile Tyr Thr Val Gly
65                  70                  75                  80

Arg Ser Phe Glu Gly Arg Glu Leu Leu Val Ile Glu Leu Ser Asp Asn
                85                  90                  95

Pro Gly Val His Glu Pro Gly Pro Glu Phe Lys Tyr Ile Gly Asn
            100                 105                 110

Met His Gly Asn Glu Ala Val Gly Arg Glu Leu Leu Ile Phe Leu Ala
            115                 120                 125

Gln Tyr Leu Cys Asn Glu Tyr Gln Lys Gly Asn Glu Thr Ile Val Asn
    130                 135                 140

Leu Ile His Ser Thr Arg Ile His Ile Met Pro Ser Leu Asn Pro Asp
145                 150                 155                 160

Gly Phe Glu Lys Ala Ala Ser Gln Pro Gly Glu Leu Lys Asp Trp Phe
                165                 170                 175

Val Gly Arg Ser Asn Ala Gln Gly Ile Asp Leu Asn Arg Asn Phe Pro
            180                 185                 190

Asp Leu Asp Arg Ile Val Tyr Val Asn Glu Lys Glu Gly Gly Pro Asn
        195                 200                 205

Asn His Leu Leu Lys Asn Leu Lys Lys Ile Val Asp Gln Asn Ser Lys
    210                 215                 220

Leu Ala Pro Glu Thr Lys Ala Val Ile His Trp Ile Met Asp Ile Pro
225                 230                 235                 240

Phe Val Leu Ser Ala Asn Leu His Gly Gly Asp Leu Val Ala Asn Tyr
                245                 250                 255

Pro Tyr Asp Glu Thr Arg Ser Gly Thr Ala His Glu Tyr Ser Ser Cys
            260                 265                 270

Pro Asp Asp Ala Ile Phe Gln Ser Leu Ala Arg Ala Tyr Ser Ser Phe
        275                 280                 285

Asn Pro Val Met Ser Asp Pro Asn Arg Pro Pro Cys Arg Lys Asn Asp
    290                 295                 300

Asp Asp Ser Ser Phe Val Asp Gly Thr Thr Asn Gly Gly Ala Trp Tyr
305                 310                 315                 320

Ser Val Pro Gly Gly Met Gln Asp Phe Asn Tyr Leu Ser Ser Asn Cys
                325                 330                 335

Phe Glu Ile Thr Val Glu Leu Ser Cys Glu Lys Phe Pro Pro Glu Glu
            340                 345                 350

Thr Leu Lys Ser Tyr Trp Glu Asp Asn Lys Asn Ser Leu Ile Ser Tyr
        355                 360                 365

Leu Glu Gln Ile His Arg Gly Val Lys Gly Phe Val Arg Asp Leu Gln
    370                 375                 380
```

```
Gly Asn Pro Ile Ala Asn Ala Thr Ile Ser Val Asp Gly Ile Asp His
385                 390                 395                 400

Asp Val Thr Ser Ala Lys Asp Gly Asp Tyr Trp Arg Leu Leu Ala Pro
                405                 410                 415

Gly Asn Tyr Lys Leu Thr Ala Ser Ala Pro Gly Tyr Leu Ala Ile Thr
            420                 425                 430

Lys Lys Val Ala Val Pro Phe Ser Pro Ala Val Gly Val Asp Phe Glu
        435                 440                 445

Leu Glu Ser Phe Ser Glu Arg Lys Glu Glu Lys Glu Glu Leu Met
    450                 455                 460

Glu Trp Trp Lys Met Met Ser Glu Thr Leu Asn Phe
465                 470                 475

<210> SEQ ID NO 15
<211> LENGTH: 434
<212> TYPE: PRT
<213> ORGANISM: Alysia

<400> SEQUENCE: 15

Arg Pro Gln Glu Asp Gly Ile Ser Phe Glu Tyr His Arg Tyr Pro Glu
1               5                   10                  15

Leu Arg Glu Ala Leu Val Ser Val Trp Leu Gln Cys Ala Ala Val Ser
            20                  25                  30

Arg Ile Tyr Thr Val Gly Arg Ser Phe Glu Gly Arg Glu Leu Leu Val
        35                  40                  45

Leu Glu Leu Ser Asp Asn Pro Gly Val His Glu Pro Gly Glu Pro Glu
    50                  55                  60

Phe Lys Tyr Ile Gly Asn Met His Gly Asn Glu Ala Val Gly Arg Glu
65                  70                  75                  80

Leu Leu Ile Phe Leu Ala Gln Tyr Leu Cys Asn Glu Tyr Gln Lys Gly
                85                  90                  95

Asn Glu Thr Ile Val Gln Leu Ile His Asn Thr Arg Ile His Ile Met
            100                 105                 110

Pro Ser Leu Asn Pro Asp Gly Phe Glu Lys Ala Ala Ser Gln Leu Gly
        115                 120                 125

Glu Leu Lys Asp Trp Phe Val Gly Arg Ser Asn Ala Gln Gly Ile Asp
    130                 135                 140

Leu Asn Arg Asn Phe Pro Asp Leu Asp Arg Ile Val Tyr Ile Asn Glu
145                 150                 155                 160

Lys Glu Gly Gly Pro Asn Asn His Leu Leu Lys Asn Leu Lys Lys Ile
                165                 170                 175

Val Asp Gln Asn Thr Lys Leu Ala Pro Glu Thr Lys Ala Val Ile His
            180                 185                 190

Trp Ile Met Asp Ile Pro Phe Val Leu Ser Ala Asn Leu His Gly Gly
        195                 200                 205

Asp Leu Val Ala Asn Tyr Pro Tyr Asp Glu Thr Arg Ser Gly Ser Ala
    210                 215                 220

His Glu Tyr Ser Ser Cys Pro Asp Asp Ile Phe Gln Ser Leu Ala
225                 230                 235                 240

Arg Ala Tyr Ser Ser Phe Asn Pro Pro Met Ser Asp Pro Asp Arg Pro
                245                 250                 255

Pro Cys Arg Lys Asn Asp Asp Ser Ser Phe Val Glu Gly Thr Thr
            260                 265                 270
```

-continued

Asn Gly Ala Ala Trp Tyr Ser Val Pro Gly Gly Met Gln Asp Phe Asn
        275                 280                 285

Tyr Leu Ser Ser Asn Cys Phe Glu Ile Thr Val Glu Leu Ser Cys Glu
        290                 295                 300

Lys Phe Pro Pro Glu Glu Thr Leu Lys Asn Tyr Trp Glu Asp Asn Lys
305                 310                 315                 320

Asn Ser Leu Ile Ser Tyr Ile Gln Gln Ile His Arg Gly Val Lys Gly
                325                 330                 335

Phe Val Arg Asp Leu Gln Gly Asn Pro Ile Ala Asn Ala Thr Leu Ser
            340                 345                 350

Val Glu Gly Ile Asp His Asp Val Thr Ser Ala Lys Asp Gly Asp Tyr
        355                 360                 365

Trp Arg Leu Leu Val Pro Gly Asn Tyr Lys Leu Thr Ala Ser Ala Pro
370                 375                 380

Gly Tyr Leu Ala Ile Ala Lys Lys Val Ala Val Pro Tyr Ser Pro Ala
385                 390                 395                 400

Val Arg Val Asp Phe Glu Leu Glu Ser Phe Glu Arg Lys Glu Glu
                405                 410                 415

Glu Lys Glu Glu Leu Met Glu Trp Trp Lys Met Met Ser Glu Thr Leu
            420                 425                 430

Asn Phe

<210> SEQ ID NO 16
<211> LENGTH: 1365
<212> TYPE: DNA
<213> ORGANISM: Lophius americanus

<400> SEQUENCE: 16

```
atgaagcaga tctgctccat agttttactg ggggccgcgg tggtctccct ggtcagcgca    60
gcggggagcg acagtgagat ctccttcgag tataccgtt atgaggagct acggaaggct    120
ctggtgtcgg tgtggctgca gtgtcccacc atcgcgcgca tctacaccat ggggagagc    180
ttcgagggcc gcgagctgct ggtactggag atgtccgaca ccccgggac gcacgaacct    240
ggtgagcctg agttcaaata cattgcgaac atgcatggca cgaggctgt tggcagagag    300
ttgctcatct acctggctca gtacctgtgc aatcagtacc agcaaggcaa cgagaccatc    360
atcgacctca tccacagcac ccgcatccac cttatgccct ccatgaaccc agatggattt    420
gagaaggctg cttctcagcc tggtgagatc aaagattggt ttgtgggccg cagtaacgca    480
cagggagtgg atctgaaccg gaacttcccg gatctgaccg tatcatcta caccaacgaa    540
cgggagggtg gtgctaacaa ccacctgctg cagaacatga agaaggctgt agatgaaaac    600
accaagctag ctccagagac aaaggcagtg atccactgga tcatggaaat ccccttcgtc    660
ctttccgcta acctgcatgg tggagatgtg gtggccaact acccatatga tgagactcgc    720
actggctcca cccacgagta cagcgccagt ccagatgacg tgatattcaa gtctctggca    780
aaggccttct ccatctacaa cccagttatg tctgaccctc agcgaccccc ctgtcgtaag    840
cacgatgatg actccagctt caaagatggc atcactaatg gaggtgcctg gtatagtgta    900
ccaggaggaa tgcaggattt caactacctt agcagcaact gctttgaaat caccttggag    960
cttagctgtg acaagttccc caatgaggat acactcaaga catactggga gcaaaaccgc    1020
aactcactgg tcaattacat cgaacaggtt catcgtggcg tcaagggcta tgtgcgtgac    1080
cttcagggca atccaatttt caatgccact atctctgttg agggcatcga ccatgacata    1140
accacagcca agacggaga ttactggcgc cttttgcgtc aaggaaatta taaggtggca    1200
```

-continued

```
gcctctgcgc cgggatacct gactgttatc aaaaaggtgg ctgtacctca cagccctgca    1260
accagggtgg actttgagct ggagtctctg atggagagga aggaggagga gcgggaggag    1320
ctgatggact ggtggaagat gatgtcagag acactgaact tctaa                   1365
```

<210> SEQ ID NO 17
<211> LENGTH: 454
<212> TYPE: PRT
<213> ORGANISM: Lophius americanus

<400> SEQUENCE: 17

```
Met Lys Gln Ile Cys Ser Ile Val Leu Leu Gly Ala Ala Val Val Ser
1               5                   10                  15

Leu Val Ser Ala Ala Gly Ser Asp Ser Glu Ile Ser Phe Glu Tyr His
                20                  25                  30

Arg Tyr Glu Glu Leu Arg Lys Ala Leu Val Ser Val Trp Leu Gln Cys
            35                  40                  45

Pro Thr Ile Ala Arg Ile Tyr Thr Ile Gly Ser Phe Glu Gly Arg
        50                  55                  60

Glu Leu Leu Val Leu Glu Met Ser Asp Asn Pro Gly Thr His Glu Pro
65                  70                  75                  80

Gly Glu Pro Glu Phe Lys Tyr Ile Ala Asn Met His Gly Asn Glu Ala
                85                  90                  95

Val Gly Arg Glu Leu Leu Ile Tyr Leu Ala Gln Tyr Leu Cys Asn Gln
            100                 105                 110

Tyr Gln Gln Gly Asn Glu Thr Ile Ile Asp Leu Ile His Ser Thr Arg
        115                 120                 125

Ile His Leu Met Pro Ser Met Asn Pro Asp Gly Phe Glu Lys Ala Ala
130                 135                 140

Ser Gln Pro Gly Glu Ile Lys Asp Trp Phe Val Gly Arg Ser Asn Ala
145                 150                 155                 160

Gln Gly Val Asp Leu Asn Arg Asn Phe Pro Asp Leu Asp Arg Ile Ile
                165                 170                 175

Tyr Thr Asn Glu Arg Glu Gly Gly Ala Asn Asn His Leu Leu Gln Asn
            180                 185                 190

Met Lys Lys Ala Val Asp Glu Asn Thr Lys Leu Ala Pro Glu Thr Lys
        195                 200                 205

Ala Val Ile His Trp Ile Met Glu Ile Pro Phe Val Leu Ser Ala Asn
    210                 215                 220

Leu His Gly Gly Asp Val Val Ala Asn Tyr Pro Tyr Asp Glu Thr Arg
225                 230                 235                 240

Thr Gly Ser Thr His Glu Tyr Ser Ala Ser Pro Asp Asp Val Ile Phe
                245                 250                 255

Lys Ser Leu Ala Lys Ala Phe Ser Ile Tyr Asn Pro Val Met Ser Asp
            260                 265                 270

Pro Gln Arg Pro Pro Cys Arg Lys His Asp Asp Ser Ser Phe Lys
        275                 280                 285

Asp Gly Ile Thr Asn Gly Gly Ala Trp Tyr Ser Val Pro Gly Gly Met
    290                 295                 300

Gln Asp Phe Asn Tyr Leu Ser Ser Asn Cys Phe Glu Ile Thr Leu Glu
305                 310                 315                 320

Leu Ser Cys Asp Lys Phe Pro Asn Glu Asp Thr Leu Lys Thr Tyr Trp
                325                 330                 335

Glu Gln Asn Arg Asn Ser Leu Val Asn Tyr Ile Glu Gln Val His Arg
            340                 345                 350
```

-continued

```
Gly Val Lys Gly Tyr Val Arg Asp Leu Gln Gly Asn Pro Ile Phe Asn
        355                 360                 365

Ala Thr Ile Ser Val Glu Gly Ile Asp His Asp Ile Thr Thr Ala Lys
        370                 375                 380

Asp Gly Asp Tyr Trp Arg Leu Leu Arg Gln Gly Asn Tyr Lys Val Ala
385                 390                 395                 400

Ala Ser Ala Pro Gly Tyr Leu Thr Val Ile Lys Lys Val Ala Val Pro
                405                 410                 415

His Ser Pro Ala Thr Arg Val Asp Phe Glu Leu Glu Ser Leu Met Glu
            420                 425                 430

Arg Lys Glu Glu Arg Glu Glu Leu Met Asp Trp Trp Lys Met Met
        435                 440                 445

Ser Glu Thr Leu Asn Phe
    450
```

METHODS OF ASSESSING WOLFRAMIN PROTEIN ACTIVITY

CROSS REFERENCE TO RELATED APPLICATIONS

This application claims the benefit of the following provisional application: application Ser. No. 60/266,385 filed Feb. 2, 2001 under 35 U.S.C 119(e)(1).

FIELD OF THE INVENTION

The present invention relates generally to the field of molecular biology. More particularly, the present invention relates to methods of assaying modulators of the interaction between Wolframin protein and a cellular binding partner which we have identified.

BACKGROUND OF THE INVENTION

Wolfram's Syndrome and Wolframin

Wolfram Syndrome (WFS) or DIDMOAD (MIM222300) is an autosomal recessive disorder most frequently characterized by Diabetes Insipidis, juvenile Diabetes Mellitus, bilateral Optic Atrophy and sensoneural Deafness (Strom et al., *Hum. Mol. Genetics.* 7(13) 2021, 1998). Minimally, individuals presenting this syndrome have diabetes mellitus and optic atrophy, however, diabetes insipidous sensorineuronal deafness, urinary tract atony, ataxia, peripheral neuropathy, mental retardation and psychiatric illness also are observed in the vast majority of patients. A range of psychiatric conditions also have been associated with WFS, including dementia, psychosis, affective disorder, major depressive disorder, suicide and assaultive behavior. (Owen, *Mol. Psychiatry,* 3, 12, 1998; Swift et al., *Am. J. Psychiatry,* 148, 775, 1991).

Recently, WFS was linked to markers on chromosome 4p. On the basis of meiotic recombinant and disease associated haplotypes, the WFS1 gene was identified as Wolframin (WFS1). This gene codes for a predicted transmembrane protein (Wolframin protein) which is expressed in a variety of tissues including the brain and pancreas. The human transmembrane protein was described in 1998 (Strom et al., supra and Inoue et al. *Nature Genetics* 20, 121, 1998). The 890 amino acid protein corresponds to a predicted molecular weight of 100 kDa.

Loss of function mutations in both alleles of this gene are associated with the disease characteristics of WFS (Inoue et al., supra; Strom et al., supra). While the homozygous loss of function mutations in the WFS1 gene have been associated with WFS, individuals that are blood relatives of individuals manifesting WFS have a 26 fold greater predisposition to psychiatric illness, including depression and depressive disorders, than those individuals that are not genetically related to individuals suffering with WFS. The odds ratio reported, 26, estimates the risk of psychiatric hospitalization (for paraonoid delusions, progressive dementia, attempted suicides, hallucinations and violent and assaultive behavior, but most notably for depression) for a Wolfram syndrome gene carrier compared to a non-carrier. Given this estimate and the estimate that Woram syndrome heterozygotes are 1% of the population, carriers of the gene maybe constitute approximately 25% of all persons hospitalized with similar psychiatric difficulties. (Swift et al., *Mol. Psychiatry,* 3, 86–91, 1998).

Wolframin protein by virtue of the convincing genetic evidence presented above is associated with a variety of health problems including diabetes insipidis, diabetes mellitus, and depression. While treatment of all diseases associated with Wolframin protein dysfunction are problematic, the treatment of depression poses particular difficulties. Numerous compounds have been developed to treat depression including for example serotonin re-uptake inhibitors (SSRI), such as sertraline (registered trademark ZOLOFT, Pfizer), fluoxetine (PROZAC—Eli Lilly), paroxetine (PAXIL—Smith Kline Beecham) and fluvoxamine (LWOX); tricyclic antidepressants such as ELAVIL (Merck, Sharpe and Dohme), aminoketone antidepressants such as bupropion, and lithium, a metal used to treat bipolar disorder. However, these drugs are very potent, often generating problematic side effects such as lethargy, clouded thinking and a lack of ability to concentrate. A pressing need exists therefore for the identification of new molecular targets and assays employing those targets as methods of identifying compounds useful in the treatment of depression and other Wolframin protein associated diseases. The heretofore undisclosed assays detailed below address this need by providing for the assessment of small molecule modulators of the functional characteristics of the Wolframin protein.

REFERENCES CITED

Patent Documents

U.S. Patents
1. U.S. Pat. No. 6,248,527, Chen, H. and Meyer, J.
2. U.S. Pat. No. 6,316,223, Payan, D., Luo, Y., and Huang, B.
3. U.S. Pat. No. 6,251,676, Shioda, T., Isselbacher, K. J.

Other Patent Documents
1. WO0023784 Chen, H. and Meyer, J.

Journal Articles

1. Bartel, P., Chien, C. T., Sternglanz, R., and Fields, S. (1993) *Biotechniques* 14(6), 920-4.
2. Che, F. Y., Yan, L., Li, H., Mzhavia, N., Devi, L. A., and Fricker, L. D. (2001) *Proc Natl Acad Sci U S A* 98(17), 9971-6.
3. Chien, C. T., Bartel, P. L., Sternglanz, R., and Fields, S. (1991) *Proc Natl Acad Sci U S A* 88(21), 9578-82.
4. Cool, D. R., Normant, E., Shen, F., Chen, H. C., Pannell, L., Zhang, Y., and Loh, Y. P. (1997) *Cell* 88(1), 73–83.
5. Dang, C. V., Barrett, J., Villa-Garcia, M., Resar, L. M., Kato, G. J., and Fearon, E. R. (1991) *Mol Cell Biol* 11(2), 954-62.
6. Dove, S. L., Joung, J. K., and Hochschild, A. (1997) *Nature* 386(6625), 627-30.
7. Durfee, T., Becherer, K., Chen, P. L., Yeh, S. H., Yang, Y., Kilburn, A. E., Lee, W. H., and Elledge, S. J. (1993) *Genes Dev* 7(4), 555-69.
8. Fields, S., and Song, 0. (1989) *Nature* 340(6230), 245-6.
9. Fricker, L. D., and Snyder, S. H. (1983) *J Biol Chem* 258(18), 10950-5.
10. Fricker, L. D. (1988) *J Cell Biochem* 38(4), 279-89.
11. Gabreels, B. A., Swaab, D. F., de Kleijn, D. P., Dean, A., Seidah, N. G., Van de Loo, J. W., Van de Ven, W. J., Martens, G. J., and Van Leeuwen, F. W. (1998) *J Clin Endocrinol Metab* 83(11), 4026-33.
12. Hannon, G. J., Demetrick, D., and Beach, D. (1993) *Genes Dev* 7(12A), 2378-91.
13. Hardy, C. F., Sussel, L., and Shore, D. (1992) *Genes Dev* 6(5), 801-14.

14. Harper, J. W., Adami, G. R., Wei, N., Keyomarsi, K., and Elledge, S. J. (1993) *Cell* 75(4), 805-16.
15. Inoue, H., Tanizawa, Y., Wasson, J., Behn, P., Kalidas, K., Bernal-Mizrachi, E., Mueckler, M., Marshall, H., Donis-Keller, H., Crock, P., Rogers, D., Mikuni, M., Kumashiro, H., Higashi, K., Sobue, G., Oka, Y., and Permutt, M. A. (1998) *Nat Genet* 20(2), 143-8.
16. Kadonaga, J. T., and Tjian, R. (1986) *Proc Natl Acad Sci U S A* 83(16), 5889-93.
17. Kohler, G., and Milstein, C. (1975) *Nature* 256(5517), 495-7.
18. Le Douarin, B., Pierrat, B., vom Baur, E., Chambon, P., and Losson, R. (1995) *Nucleic Acids Res* 23(5), 876-8.
19. Luban, J., Bossolt, K. L., Franke, E. K., Kalpana, G. V., and Goff, S. P. (1993) *Cell* 73(6), 1067-78.
20. Manser, E., Fernandez, D., Loo, L., Goh, P. Y., Monfries, C., Hall, C., and Lim, L. (1990) *Biochem J* 267(2), 517-25.
21. Owen, M. J. (1998) *Mol Psychiatry* 3(1), 12-3.
22. Parodi, L. A., Granatir, C. A., and Maggiora, G. M. (1994) *Comput Appl Biosci* 10(5), 527-35.
23. Silver, S. C., and Hunt, S. W., 3rd. (1993) *Mol Biol Rep* 17(3), 155-65.
24. Sonnhammer, E. L., von Heijne, G., and Krogh, A. (1998) *Proc Int Conf Intell Syst Mol Biol* 6, 175-82.
25. Strom, T. M., Hortnagel, K., Hofmann, S., Gekeler, F., Scharfe, C., Rabl, W., Gerbitz, K. D., and Meitinger, T. (1998) *Hum Mol Genet* 7(13), 2021-8.
26. Swift, R. G., Perkins, D. O., Chase, C. L., Sadler, D. B., and Swift, M. (1991) *Am J Psychiatry* 148(6), 775-9.
27. Swift, R. G., Polymeropoulos, M. H., Torres, R., and Swift, M. (1998) *Mol Psychiatry* 3(1), 86–91.
28. Varlamov, O., Leiter, E. H., and Fricker, L. (1996) *J Biol Chem* 271(24), 13981-6.
29. Vojtek, A. B., Hollenberg, S. M., and Cooper, J. A. (1993) *Cell* 74(1), 205-14.
30. Yang, X., Hubbard, E. J., and Carlson, M. (1992) *Science* 257(5070), 680-2.
31. Zervos, A. S., Gyuris, J., and Brent, R. (1993) *Cell* 72(2), 223-32.

BRIEF DESCRIPTION OF THE SEQUENCE LISTING

SEQ ID NO:1 human wolframin cDNA coding sequence (derived from Genbank Accession # AF08448 1)
SEQ ID NO:2 human wolframin polypeptide sequence (Genbank Accession # AF084481)
SEQ ID NO:3 human carboxypeptidase E cDNA coding sequence (derived from Genbank Accession # NM_001873)
SEQ ID NO:4 human carboxypeptidase E polypeptide sequence (Genbank Accession # NP_001864)
SEQ ID NO:5 PCR Primer—Example 1
SEQ ID NO:6 PCR Primer—Example 1
SEQ ID NO:7 rat wolframin cDNA coding sequence (derived from Genbank Accession # NM_031823, AF136378)
SEQ ID NO:8 rat wolframin polypeptide sequence (Genbank Accession # AF136378_1)
SEQ ID NO:9 mouse wolframin cDNA coding sequence (derived from Genbank Accession # NM_011716, AJ011971)
SEQ ID NO:10 mouse wolframin polypeptide sequence (Genbank Accession # NP_035846, CAA09892)
SEQ ID NO:11 rat carboxypeptidase E cDNA coding sequence (derived from Genbank Accession # NM_013128, X51406)
SEQ ID NO:12 rat carboxypeptidase E polypeptide sequence (Genbank Accession # NP_037260, CAA35768, 99% identical to sequence disclosed in WO0023784 and U.S. Pat. No. 6,248,527)
SEQ ID NO:13 mouse carboxypeptidase E cDNA coding sequence (derived from Genbank Accession # BC010197)
SEQ ID NO:14 mouse carboxypeptidase E polypeptide sequence (Genbank Accession # AAH10197)
SEQ ID NO:15 alysia carboxypeptidase E polypeptide sequence (Disclosed in WO0023784 and U.S. Pat. No. 6,248,527)
SEQ ID NO:16 lophius americanus (anglerfish) carboxypeptidase E cDNA coding sequence (derived from Genbank Accession # U01909, S80565)
SEQ ID NO:17 lophius americanus (anglerfish) carboxypeptidase E polypeptide sequence (derived from Genbank Accession AAC59636, S80565, disclosed in WO0023784 and U.S. Pat. No. 6,248,527)

SUMMARY OF THE INVENTION

The invention provides a method for identifying agents that modulate the propensity of a Wolframin protein polypeptide to associate with a carboxypeptidase E binding partner polypeptide comprising: (a) contacting said Wolframin protein polypeptide and said carboxypeptidase E binding partner polypeptide in the presence and absence of a test agent; (b) and determining the propensity of said Wolframin protein polypeptide to associate with a said binding carboxypeptidase E partner polypeptide in the presence and absence of the test agent; and (c) comparing the propensity of said Wolframin protein polypeptide to associate with said carboxypeptidase E binding partner polypeptide in the presence of the test agent with the propensity of said Wolframin protein polypeptide to associate with a said carboxypeptidase E binding partner polypeptide in the absence of the test agent.

The invention further provides a method of identifying agents which modulate the propensity of a Wolframin protein polypeptide to associate with a carboxypeptidase E binding partner polypeptide comprising the steps of: (a) contacting a cell with a test compound, wherein the cell comprises: i) a first fusion protein comprising a DNA binding domain and a Wolframin protein polypeptide ii) a second fusion protein comprising a transcriptional activating domain and a carboxypeptidase E protein or carboxypeptidase E protein fragment; wherein the interaction of the Wolframin protein polypeptide with the carboxypeptidase E protein or carboxypeptidase E protein fragment reconstitutes a sequence specific transcriptional activating factor; and iii) a reporter gene comprising a DNA sequence to which the DNA binding domain of the first fusion protein specifically binds; and (b) measuring the expression of the reporter gene, wherein a test compound that changes the level of expression of the reporter gene would be a potential drug for modulating Wolframin activity.

The invention further provides a method of identifying agents which modulate the propensity of a Wolframin protein polypeptide to associate with a carboxypeptidase E binding partner polypeptide comprising the steps of: (a) contacting a cell with a test compound, wherein the cell comprises: i) a first fusion protein comprising a transcriptional activating domain and a Wolframin protein polypeptide ii) a second fusion protein comprising a DNA binding domain and a carboxypeptidase E protein or carboxypeptidase E protein fragment; wherein the interaction of the Wolframin protein polypeptide with the carboxypeptidase E protein or carboxypeptidase E protein fragment reconstitutes a sequence specific transcriptional activating factor; and iii) a reporter gene comprising a DNA sequence to which the DNA binding domain of the first fusion protein specifically binds; and (b) measuring the expression of the reporter gene; wherein a test compound that changes the level of expression of the reporter gene would be a potential drug for modulating Wolframin activity.

An agent that increases the propensity for Wolframin to associate with its binding partner is a potential drug for increasing Wolframin protein activity. A test compound that decreases the propensity for Wolframin to associate with its binding partner is a potential drug for decreasing Wolframin protein activity.

DETAILED DESCRIPTION OF THE INVENTION

Because of the multiplicity neuroendocrine disturbances in patients presenting with Wolframin syndrome and those heterozygous for an altered Wolframin protein locus it has been postulated that Wolframin protein somehow plays a role in the processing of preprohormones. (Gabreels et al. J. Clin. Endocrinol Matab. 83(11) 4026-33 (1998).

We have recently made the exciting discovery that Wolframin protein associates with carboxypeptidase E in vivo and that the interaction has physiologic significance. Carboxypeptidase E, known also as carboxypeptidase H and enkephalin convertase, is involved in the processing of various bioactive peptides including peptide hormones and neurotransmitters (Fricker, in Peptide Biosynthesis and Processing) Fricker, ed. (pages 199–230 CRC Press, Boca Raton, Fla.) (1991). Many peptide hormones and neurotransmitters are initially produced as precursors that are enzymatically processed into bioactive peptides (Fricker J. Cell Biochem. 38:279–289 (1988)). Initially, prohormone convertases cleave the prohormone precursor at multiple basic amino acid cleavage sites (Varlamov et al. J. Biochem. 271:13981-13986) (1996). In general the site of proteolysis can be described by the consensus site (basic)$X_n$(basic), where X is any amino acid(s) other than Cys and n is 0, 2, 4 or 6. In general the prohormone convertases cleave at the C terminal side of the basic residues. A carboxypeptidase (principally CPE) then removes the basic amino acids from the C terminus of the peptide to generate either the bioactive product or a precursor to form the C-terminal amide group. This process is important for the production of bioactive peptides in many tissues. Carboxypeptidase E is present in many tissues where peptide biosynthesis occurs including brain, pituitary, and adrenal medulla (Fricker, J. Cell. Biochem., supra). The activity is localized to secretory granules where carboxypeptidase E exists in membrane and soluble forms (Manser et al. Biochem. J. 267:517–525 (1990)). Carboxypeptidase E does not appear to contain a transmembrane-spanning helical region, which suggests that carboxypeptidase E is membrane bound through another mechanism.

A mouse model of carboxypeptidase E dysfunction ($Cpe^{fat}/Cpe^{fat}$) has been described (Che et al. PNAS 98, 9971–9976 (2001)). In $Cpe^{fat}/Cpe^{fat}$ mice a point mutation in carboxypeptidase E ($Ser^{202}\rightarrow Pro$) leads to inactivation of the enzyme and degradation of carboxypeptidase E. The absence of carboxypeptidase activity causes the accumulation of C-terminally extended insulins, enkephalins, and other neuroendocrine peptides. Most of the identified peptides in brain arose from six proteins; proopiomelanocortin (POMC), proenkephalin, chromogranin B, secretogranin II, provasoppressin, and proSAAS. Current theories of the pathology of depression suggests that it results from dysfunctional adaptive responses to stress resulting in reduced neuronal plasticity and the atrophy and death of neurons in the hippocampus and prefrontal cortex. Neuropeptides play a crucial role in the adaptation and plasticity of neurons in response to stress and any impairment of the processing or secretion of these survival factors could result in predisposition to depression. (Duman R S et al. Biol. Psychiatry 46, 1181-91 (1999)). Increasing neuropeptide secretion in response to stress could restore neural plasticity by increase cell survival and function.

Recently interest has been generated by the proposal that carboxypeptidase E serves as a sorting receptor in neuroendocrine cells. The hypothesis is that carboxypeptidase E might control entry into secretory granules in a manner that is entirely independent of its enzymatic activity. The receptor like properties of carboxypeptidase E were largely inferred by identification its binding to the N terminus of POMC and by competitive displacement of this interaction by several regulated secretory proteins (proinsulin, proenkephalin and chromogranin A) but not by constitutive secretory proteins. (Cool et al. Cell, 88, 73–83, (1997)).

Our own experiments have specifically validated the functional relevance of the Wolframin protein, carboxypeptidase E interaction. It is known that membrane depolarization of PC12 cells results in carboxypeptidase E secretion. When Rat PC-12 cells were transfected with expression vectors encoding a Wolframin mutant polypeptide truncated at amino acid 136 regulated secretion of carboxypeptidase E was abolished.

We have also shown via immunohistochemical staining with antisera directed against Wolframin protein and carboxypeptidase E and in situ mRNA localization in rat brain slices that both proteins are found in common regions including the hippocampus, hypothalamus, amygdala and substantial nigra. When confocal miscroscopy is performed with labeled antisera directed to carboxypeptidase E and Wolframin protein we have demonstrated colocalization of the two proteins. Punctate staining suggesting localization in the endoplasmic reticulum (ER).

We have also used antisera to Wolframin protein to compare staining patterns in the hippocampus of depressed vs. normal human autopsy brains. Similar staining was observed in the neurons of both control and depressed brains, but staining of astrocytes was observed in 2 of 3 depressed brains, but in none of 3 controls. This suggests a disregulation of Wolframin localization in the hippocampus of depressed individuals. Because these patients were not known to harbor Wolframin protein mutations it suggests that depression might be ameliorated even in those having an unaltered Wolframin protein gene, by enhancing the interaction between Wolframin protein and carboxypeptidase E. The methods of the invention therefore encompass the use of both wild-type as well as mutant wolframin proteins.

General Definitions

The term "about" is used herein when describing fragments of a polypeptide chain. In this context "about" includes the particularly recited range and ranges larger or smaller by several, a few, 9, 8, 7, 6, 5, 4, 3, 2 or 1 amino acid residues at either extreme or at both extremes. By way of example, there may be mentioned polypeptides which comprise "about" the first 100 amino terminal amino acids of a reference sequence. Such a polypeptide would comprise a polypeptide which has deleted several, a few, 9, 8, 7, 6, 5, 4, 3, 2 or 1 amino acid residues from the amino terminus and contains either plus or minus several, a few, 9, 8, 7, 6, 5, 4, 3, 2 or 1 amino acid residues at the carboxy terminus.

"Carboxypeptidase E" as used herein means a polypeptide species 99%, at least 95%, at least 90%, at least 85%, at least 80%, at least 75%, at least 70%, at least 65%, at least 60%, at least 55% or at least 50% identity and/or homology over its entire length to the polypeptide set out in SEQ ID NO: 4. A preferred embodiment is a polypeptide species having at least 75% sequence identity with SEQ ID NO:4.

Percent amino acid sequence "identity" with respect to the polypeptide of SEQ ID NO: 4 is defined herein as the percentage of amino acid residues in the candidate sequence that are identical with the residues in the carboxypeptidase E sequence after aligning both sequences and introducing gaps, if necessary, to achieve the maximum percent sequence identity, and not considering any conservative substitutions as part of the sequence identity. The term "carboxypeptidase E" or "carboxypeptidase E polypeptide" is intended to encompass "carboxypeptidase E binding partner polypeptides" as described below. When percent identity is calculated for "carboxypeptidase E binding partner polypeptides" that are shorter than the full length of SEQ ID NO:4 it is done so without regard to the unmatched amino acids not encompassed within the fragment.

Percent sequence "homology" with respect to the polypeptide of SEQ ID NO: 4 is defined herein as the percentage of amino acid residues in the candidate sequence that are identical with the residues in the carboxypeptidase E sequence after aligning the sequences and introducing gaps, if necessary, to achieve the maximum percent sequence identity, and also considering any conservative substitutions as part of the sequence identity. Percent homology is calculated as the percentage of amino acid residues in the smaller of two sequences which align with identical amino acid residue in the sequence being compared, when four gaps in a length of 100 amino acids may be introduced to maximize alignment [Dayhoff, in Atlas of Protein Sequence and Structure, Vol. 5, p. 124, National Biochemical Research Foundation, Washington, D.C. (1972), incorporated herein by reference]. The term "Carboxypeptidase E" as defined herein therefore, encompasses species homologs, sometimes referred to as "orthologs," of the human protein. The rat, murine, alysia, and lophius orthologs are exemplified herein and are represented as SEQ ID NOS: 12, 14, 15 and 17 respectively. It should be noted that the carboxypeptidase E amino acid sequence is highly conserved and that most known orthologs share considerable sequence homology with the human protein. The rat, murine, alysia, and lophius orthologs of carboxypeptidase E have approximately 96%, 96%, 95%, and 76% identity respectively with the human amino acid sequence. (The alysia sequence is found in the databases in only its mature form but presumably exists as a longer sequence as well) The bovine sequence has been reported at Genbank accession number X04411 and appears to be the same as that reported for alysia at SEQ ID NO:15. However this bovine sequence differs considerably from the bovine sequence reported in WO0023784 and U.S. Pat. No. 6,248,527.

Because of the conserved nature of carboxypeptidase E polypeptides and nucleic acids an ordinarily skilled artisan has little difficulty in generating human or orthologous carboxypeptidase E. A preferred method is the polymerase chain reaction (PCR) of a template comprising a nucleic acid encoding the desired fragment and subsequent expression in a host cell. However, other methods including the purification of naturally occurring protein in tissue or cultured cells is contemplated.

The coding regions of polynucleotides encoding the human, rat, mouse and lophius carboxypeptidase E proteins are disclosed herein as SEQ ID NOS: 3, 11, 13, 16,. It should be noted that the rat, mouse and lophius encoding cDNA's are approximately 88, 88 and 70% identical to the human sequence. The ordinarily skilled artisan recognizes that because the polynucleotides encoding Wolframin protein are so conserved other orthologous species are easily obtainable either by designing suitable PCR primers from completely conserved areas or by the use of degenerate oligonucleotides.

The term "carboxypeptidase E binding partner polypeptide" as used herein means at least 50 contiguous amino acids, preferably at least 100 contiguous amino acids, more preferably at least 150 contiguous amino acids, and most preferably at least 200 or more contiguous amino acids of carboxypeptidase E (as defined above). wherein the fragment is capable of interacting with a Wolframin protein polypeptide and where the interaction is sufficiently strong to permit measurement of the association. It should be noted that by definition the term "carboxypeptidase E binding partner polypeptide" encompasses full length "carboxypeptidase E" (as defined above). The term "carboxypeptidase E binding partner polypeptide" includes polypeptides having the preprosequence, prosequence, and also mature forms of carboxypeptidase E as described by Song and Fricker, Biochem. J. 323, 265–271 (1997). Representative embodiments reflecting processing at the N terminus include fragments of SEQ ID NO:4, 12, 14, which include amino acid residues 28–476, 28–280, 43–280 and 43–476. Other embodiments would include the mature alysia sequence (SEQ ID NO:15) and residues 21–258, 21–454 of the lophius sequence (The lophius sequence appear not to contain a prosequence). Methods of assessing the propensity of a polypeptide to associate with another polypeptide are well known in the art and illustrative examples are discussed. As a convenience "carboxypeptidase E binding partner polypeptide" may be referred to as a "binding partner polypeptide" in this specification.

The ordinarily skilled artisan recognizes that any given "carboxypeptidase E binding partner polypeptide" can be derived from either the human protein as exemplified by SEQ ID NO:4 or orthologs of the human protein as exemplified by SEQ ID NOS: 12, 14, 15 or 17. Because of the conserved nature of carboxypeptidase E polypeptides and nucleic acids an ordinarily skilled artisan has little difficulty in generating human or orthologous carboxypeptidase E binding partner polypeptides. A preferred method is the polymerase chain reaction (PCR) of a template comprising a nucleic acid encoding the desired fragment. The ordinarily skilled artisan recognizes that because the nucleic acids encoding carboxypeptidase E proteins are so conserved other orthologous species are easily obtainable either by designing PCR primers from completely conserved areas or by the use of degenerate oligonucleotides.

The term "conservative" amino acid substitution or change as used within this invention is meant to refer to amino acid substitutions which substitute functionally equivalent amino acids. Conservative amino acid changes result in silent changes in the amino acid sequence of the resulting protein. For example, one or more amino acids of a similar polarity act as functional equivalents and result in a silent alteration within the amino acid sequence of the protein. Conservative amino acid substitution have been defined as the amino acid substitutions set forth in Table 1 on page 240 of Taylor, W. R., (1986) J. Mol. Biol. 188: 233–258. The largest sets of conservative amino acid substitutions include:

(1) hydrophobic: His, Trp, Tyr, Phe, Met, Leu, Ile, Val, Ala;
(2) neutral hydrophilic: Cys, Ser, Thr;
(3) polar: Ser, Thr, Asn, Gln;
(4) acidic/negatively charged: Asp, Glu;
(5) charged: Asp, Glu, Arg, Lys, His
(6) basic/positively charged: Arg, Lys, His;
(7) basic: Asn, Gln, His, Lys, Arg;
(8) residues that influence chain orientation: Gly, Pro; and
(9) aromatic: Trp, Tyr, Phe, His.

In addition, structurally similar amino acids can substitute for some of the specific amino acids. Groups of structurally similar amino acids include: (Ile, Leu, and Val); (Phe and Tyr); (Lys and Arg); (Gln and Asn); (Asp and Glu); and (Gly, and Ala). Exemplary conservative amino acid substitutions are preferably made in accordance with the following: Gly or Ser for Ala; Lys for Arg; Gln or His for Asn; Glu for Asp; Ser for Cys; Asn for Gln; Asp for Glu; Ala or Pro for Gly; Asn or Gln for His; Leu or Val for Ile; Ile or Val for Leu; Arg, Gln, or Glu for Met; Met, Leu or Tyr for Phe; Thr for Ser; Ser for Thr; Tyr for Trp; Trp or Phe for Tyr; Ile or Leu for Val.

As used herein, the term "contacting" means bringing together, either directly or indirectly, a test agent into physical proximity to a polypeptide used in the invention. Additionally "contacting" may mean bringing a polypeptide of the invention into physical proximity with another polypeptide used in the the invention. In the context of whole cell assays it specifically contemplated that "contacting" may include growing the cells in the presence of a test agent or may mean simply exposing the cell to the test agent in a transient fashion.

As used herein, "DNA-binding domain" means an amino acid sequence that binds specifically to a particular DNA sequence. The site where the DNA-binding domain binds is known as a DNA binding site.

"Isolated" as used herein and as understood in the art, whether referring to "isolated" polynucleotides or polypeptides, is taken to mean separated from the original cellular environment in which the polypeptide or nucleic acid is normally found. As used herein therefore, by way of example only, a protein expressed by recombinant means in a cell type in which it does not naturally occur is "isolated". By way of example, a protein species, whether expressed in a naturally occurring cell or not, when purified to any extent is "isolated".

As used hereinafter "polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "polynucleotide" also embraces relatively short polynucleotides, often referred to as oligonucleotides.

As used hereinafter "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Glycosylated and non-glycosylated form of polypeptides are embraced by this definition.

By "reporter gene" is meant a gene whose expression may be assayed; such genes include without limitation, beta-glucuronidase (GUS), luciferase, chloramphenicol transacetylase (CAT), and beta-galactosidase.

"Synthesized" or "synthetic" as used herein and understood in the art, refers to polynucleotides or polypeptides produced by purely chemical, as opposed to enzymatic, methods. "Wholly" synthesized DNA or polypeptide sequences are therefore produced entirely by chemical means, and "partially" synthesized or synthetic DNAs or polypeptides embrace those wherein only portions of the resulting DNA or polypeptide were produced by chemical means.

The term "test agent" means any means identifiable natural or synthetic chemical or molecule, including, but not limited to a small molecule, peptide, protein, sugar, nucleotide, or nucleic acid which is assessed for its ability to modulate the propensity of a Wolframin protein polypeptide to associate with a carboxypeptidase E binding partner polypeptide.

As used herein, "transcriptional activation domain" means an amino acid sequence which when in proximity to transcriptional regulatory DNA elements of a target gene, activates gene transcription.

"Woframin protein" or 'Woframin protein polypeptide' as used herein means a polypeptide species having at least 99%, at least 95%, at least 90%, at least 85%, at least 80%, at least 75%, at least 70%, at least 65%, at least 60%, at least 55% or at least 50% identity and/or homology over its entire length to the polypeptide set out in SEQ ID NO: 2 wherein the polypeptide species is capable of interacting with a carboxypeptidase E binding partner polypeptide and where the interaction is sufficiently strong to permit measurement of the interaction. While the term "Wolframin protein" or Wolframin protein polypeptide is intended to encompass fragments it also includes within its definition "full length Wolframin protein" which has been described by Strom et al., Hum. Mol. Genetics. 7(13) 2021, 1998 and A preferred embodiment is a polypeptide species having at least 80% sequence identity with SEQ ID NO:2. Another preferred embodiment is a polypeptide species having at least 85% sequence identity with SEQ ID NO:2.

Percent amino acid sequence "identity" with respect to the polypeptide of SEQ ID NO: 2 is defined herein as the percentage of amino acid residues in the candidate sequence that are identical with the residues in the Wolframin protein sequence after aligning both sequences and introducing gaps, if necessary, to achieve the maximum percent sequence identity, and not considering any conservative substitutions as part of the sequence identity. The term "Wolframin protein" or Woframin protein polypeptide is intended to encompass Wolframin protein fragments as described below. When percent identity is calculated for a Wolframin protein fragment it is done so without regard to the unmatched amino acids not encompassed within the fragment.

Percent sequence "homology" with respect to the polypeptide of SEQ ID NO: 2 is defined herein as the percentage of amino acid residues in the candidate sequence that are identical with the residues in the Wolframin protein sequence after aligning the sequences and introducing gaps, if necessary, to achieve the maximum percent sequence identity, and also considering any conservative substitutions as part of the sequence identity. Percent homology is calculated as the percentage of amino acid residues in the smaller of two sequences which align with identical amino acid residue in the sequence being compared, when four gaps in a length of 100 amino acids may be introduced to maximize alignment [Dayhoff, in Atlas of Protein Sequence and Structure, Vol. 5, p. 124, National Biochemical Research Foundation, Washington, D.C. (1972), incorporated herein by reference].

The term "Wolframin protein" as defined herein therefore, encompasses species homologs, sometimes referred to as "orthologs," of the human protein. The rat and murine orthologs are exemplified herein and are represented as SEQ ID NOS: 8 and 10 respectively. It should be noted that Wolframin protein is highly conserved and that known orthologs share considerable sequence homology with the human protein. By way of example the rat and mouse Wolframin proteins have approximately 86% identity with the human amino acid sequence.

Because of the conserved nature of Wolframin proteins and nucleic acids an ordinarily skilled artisan has little difficulty in generating human or orthologous Wolframin proteins. A preferred method is the polymerase chain reaction (PCR) of a template comprising a nucleic acid encoding the desired fragment and subsequent expression in a host cell. However, other methods including the purification of naturally occuring protein in tissue or cultured cells is contemplated.

The coding regions of polynucleotides encoding the human, rat and mouse Wolframin proteins are disclosed herein as SEQ ID NOS: 1, 7 and 9. It should be noted that the rat and mouse encoding cDNA's are approximately 84% identical to the human sequence. The ordinarily skilled artisan recognizes that because the polynucleotides encoding Wolframin protein are so conserved other orthologous species are easily obtainable either by designing suitable PCR primers from completely conserved areas or by the use of degenerate oligonucleotides.

The mutations listed in Table 1 below have been derived from samples derived from patients exhibiting either symptoms of DIDMOAD if in the homozygous state or depression or anxiety if in the heterozygous state. However, it is to be appreciated that such mutations may not be causative of a disease state. That is, other mutations in such patients outside the coding region may cause loss of Wolframin function (in promoter or regulatory regions for example). The invention is intended to make use of Wolframin protein mutants either heretofore described or newly discovered exhibiting wild type activity or as well as those resulting in modification of the functional characteristics of the protein. One goal of the present invention is to find compounds which alleviate the symptoms of Wolframin disease when such a treatment is possible (i.e. the patient makes a Wolframin protein with altered characteristics as opposed to complete loss absence of a protein) as well as finding compounds which enhance the natural function of wild type Wolframin protein

TABLE 1

Summary of Published Mutations in WS patients resulting in Amino Acid Changes

| Type of Mutation | Exon | Nucleotide Change | AA Change | Reference |
|---|---|---|---|---|
| Missense Mutations | 5 | G to A | E169K | Hardy et al |
| | 8 | C to T | P724L | Inoue et al |
| | 8 | G to T | G695V | Inoue et al |
| | 8 | C to T | PS04L | Inoue et al |
| | 8 | A to G | Y869C | Strom et al |
| | 8 | G to C | G437A | Hardy et al |
| | 8 | C to A | C736S | Hardy et al |
| | 8 | C to T | P885L | Hardy et al |
| | 8 | C to T | P292S | Hardy et al |
| | 8 | T to C | C690R | Hardy et al |
| | 8 | A to G | R456H | Inoue et al |
| | 8 | G to A | H611R | Inoue et al |
| | 8 | T to G | M312R | Torres et al |
| | 8 | G to A | M518I | Torres et al |
| | 8 | G to A | G786S | Torres et al |
| | 8 | G to A | D866N | Torres et al |
| | 8 | C to T | R558C | Torres et al |
| | 8 | C to T | R772C | Torres et al |
| | 8 | C to T | A602V | Torres et al |
| | 8 | G to A | V871M | Torres et al |
| | 8 | G to A | G576S | Torres et al |
| | 8 | C to T | R818C | Torres et al |
| | 8 | C to G | L432V | Torres et al |
| | 8 | G to A | A559T | Torres et al |
| | 8 | A to G | D771G | Torres et al |
| | 8 | G to A | V441M | Torres et al |
| | 8 | G to A | C426Y | Torres et al |
| | 8 | G to A | A559T | Torres et al |
| | 8 | G to A | A586T | Torres et al |
| | 8 | G to A | E717K | Torresetal |
| Inframe deletions/ insertions | 8 | 15 bp deletion | del508YVYLL | Inoue et al |
| | 8 | 9 bp deletion | del480 | Strom et al |
| | 8 | 24 bp insertion | ins721 | Strom et al |
| | 8 | 6 bp deletion | del567LE | Hardy et al |
| | 8 | 3 bp deletion | del415V | Hardy et al |
| | 8 | 3 bp deletion | del354F | Hardy et al |
| Nonsense Mutations | 4 | C to T | Glu136X | Strom et al |
| | 6 | C to T | Q226X | Inoue et al |
| | 8 | G to A | W648X | Hardy et al |
| | 8 | C to T | Q366X | Strom et al |
| | 8 | C to T | Q819X | Strom et al |
| | 8 | C to T | Q520X | Strom et al |
| | 8 | G to A | Trp478X | Hardy et al |
| | 8 | C to T | Gln668X | Hardy et al |
| | 8 | C to A | Tyr302X | Hardy et al |
| | 8 | C to T | Gln667X | Hardy et al |
| | 8 | G to T | Glu273X | Hardy et al |
| | 8 | G to T | Glu752X | Hardy et al |
| Frameshift insertion/deletion | 5 | 1-bp deletion | del200fs | Strom et al |
| | 8 | 2-bp deletion | del882fs/ter937 | Inoue et al |
| | 8 | 7-hp insertion | ins483fs/ter544 | Inoue et al |
| | 8 | 2-hp deletion | del508fs | Strom et al |
| | 8 | 1-hp deletion | del517fs/terS21 | Hardy et al |
| | 8 | 14-hp deletion | del537fs | Hardy et al |
| | 8 | 1-hp deletion | del812fs/ter861 | Hardy et al |
| | 8 | 4-hp deletion | readthrough/ 949 | Hardy et al |
| Splicing mutation | 4 | G to A | 5' splice signal | Strom et al |

The invention provides methods of assessing Wolframin protein function and thus provides a rapid means of assessing the functionality of naturally occurring as well as non-naturally occurring Wolframin protein mutants.

It is specifically contemplated that the invention makes use of both "Wolframin protein fragments" and full length species of Wolframin protein. The term "Wolframin protein" encompasses Wolframin protein fragments. The term "Wolframin protein fragment" as used herein means at least 50 contiguous amino acids, at least 100 contiguous amino acids, at least 150 contiguous amino acids, at least 200 contiguous amino acids, at least 250 contiguous amino acids, or at least 300 or more contiguous amino acids of Wolframin protein, wherein the fragment is capable of interacting with a carboxypeptidase E binding partner polypeptide and where the interaction is sufficiently strong to permit measurement of the association.

It is recognized that a fragment lacking transmembrane domains is often particularly useful when dealing with a protein such as Wolframin protein because of its ease of handling and enhanced solubility characteristics. Transmembrane regions can be identified by computer programs well known in the art. Two such programs are exemplified by TMHMM (Sonnhammer 1998) and TMPRED (Parodi 1994).

The transmembrane helices predicted by TMHMM and the consensus method of TMPRED are located in the following regions of the human WFS 1:

TM# TMHMM TMPRED(consensus)

| TM # | TMHMM | TMPRED (consensus) |
|------|---------|---------------------|
| I    | 311–333 | 307–326 |
| II   | 340–362 | 332–356 |
| III  | 405–423 | 402–421 |
| IV   | 430–448 | 427–446 |
| V    | 463–481 | 462–481 |
| VI   | 494–516 | 495–516 |
| VII  | 531–549 | 531–555 |
| VIII | 562–584 | 564–588 |
| IX   | 588–610 | 594–613 |
| X    | 630–652 | 629–651 |
| XI   |         | 871–890 |

A fragment lacking transmembrane domains therefore is easily designed for the human sequence as well as orthologs. Such a fragment would contain about the first 313 amino terminal amino acids. Another embodiment contains about the first 242 amino terminal amino acids. Another embodiment contains about the first 135 amino acids. Methods of assessing the propensity of a polypeptide to associate with another polypeptide are well known in the art and illustrative examples are discussed. A "Wolframin protein fragment" may comprise either wild type contiguous amino acids or may encompass one or more mutated amino acids and contiguous amino acids derived from the Wolframin protein sequence as exemplified by "Wolframin protein mutants".

The ordinarily skilled artisan recognizes that any given "Wolframin protein fragment" can be derived from either the human protein as exemplified by SEQ ID NO:2 or orthologs of the human protein as exemplified by SEQ ID NO:8 and 10. Because of the conserved nature of Wolframin proteins and nucleic acids an ordinarily skilled artisan has little difficulty in generating fragments of human or orthologous Wolframin proteins. A preferred method is the polymerase chain reaction (PCR) of a template comprising a nucleic acid encoding the desired fragment. The ordinarily skilled artisan recognizes that because the nucleic acids encoding Wolframin protein are so conserved other orthologous fragment species are easily obtainable either by designing PCR primers from completely conserved areas or by the use of degenerate oligonucleotides.

Assays of the Invention

In-Vivo Assay of the Invention

Wolframin protein is likely to physically bind to a binding partner polypeptide either in a direct manner or via a bridging molecule to mediate its effects within the cell. Thus, assays which monitor Wolframin binding partner binding are of value in screening for Wolframin protein modulators. Administration of an efficacious dose of an agent capable of specifically modulating the interaction between Wolframin protein and its natural binding partner can be used as a therapeutic or prophylactic method for treating pathological conditions (e.g., major depression, bipolar disorder, general anxiety disorder, obsessive compulsive disorder, panic disorder, diabetes insipidus, diabetes mellitus, optic atrophy and deafness) It is specifically contemplated that agents found by these methods and other methods hereinafter described will be useful for modulating the interaction of Wolframin point mutants with carboxypeptidase E as well as modulating the interaction of the wild type protein with carboxypeptidase E.

As noted above we have identified carboxypeptidase E as a binding partner for the Wolframin protein. The identity of specific proteins which interact with full length Wolframin protein or a Wolframin protein fragment could have been assessed in a variety of ways. To determine the identity of proteins that associate with Wolframin protein, we chose a yeast two-hybrid procedure with a Wolframin protein fragment as the "bait" and a cDNA library or an brain cDNA library as the "prey". While we performed such experiments to determine the identity of at least one binding partner of Wolframin protein, it should be recognized that once an interaction is determined a cell expressing both interacting species can then form the basis for a screening system to assess the ability of compounds to modulate the strength of the interaction.

The construction of yeast two-hybrid systems is generally known. This approach identifies protein-protein interactions in vivo through reconstitution of a transcriptional activator (Fields and Song (1989) Nature 340: 245). In the typical yeast 2-hybrid system, protein A is expressed as a fusion protein with the DNA binding domain of Gal4 or lexA and protein B is expressed as a fusion protein with an activation domain, typically a region of acidic amino acids derived from Gal4 or VP16. An interaction between proteins A and B reconstitutes a transactivation function that is observed by expression of a reporter gene (e.g., LacZ, HIS3, URA3). The expression of the reporter gene is regulated by the placement of Gal4 binding sites or lexA operator sites upstream of the reporter coding region.

Typically, the two hybrid method is used to identify novel polypeptide sequences which interact with known protein (Silver S C and Hunt S W (1993) Mol. Biol. Rep. 17: 155; Durfee et al. (1993) Genes Devel. 7; 555; Yang et al. (1992) Science 257: 680; Luban et al. (1993) Cell 73: 1067; Hardy et al. (1992) Genes Devel. 6; 801; Bartel et al. (1993) Biotechniques 14: 920; and Vojtek et al. (1993) Cell 74: 205). As applied to the present case, the two-hybrid system permits identification of polypeptide peptide sequences which interact with Wolframin protein, and are therefore, potential Wolframin binding partners.

Yeast comprising (1) an expression cassette encoding a GALA or lexA DNA binding domain (or GAL4 or lexA activator domain) fused to a binding fragment of Wolframin protein capable of binding to a partner protein (2) an expression cassette encoding a GAL4 DNA activator domain (or GALA or lexA binding domain, respectively) fused to a member of a cDNA library or a binding fragment of a DNA polymerase capable of binding to a mammalian DNA Wolframin protein polypeptide, and (3) a reporter gene (e.g., beta-galactosidase) comprising a cis-linked GAL4 or lexA transcriptional response element can be used for agent screening. Such yeast are incubated with a test agent and expression of the reporter gene (e.g., beta-galactosidase) is determined; the capacity of the agent to inhibit expression of the reporter gene as compared to a control culture identifies whether the candidate agent is a Wolframin modulating agent.

Yeast two-hybrid systems may be used to screen a mammalian (typically human) cDNA expression library, wherein human cDNA is fused to a GAL4 or lexA DNA binding domain or activator domain, and a Wolframin polypeptide sequence or fragment is fused to a GAL4 or lexA activator domain or DNA binding domain, respectively. Such a yeast two-hybrid system can screen for cDNAs that encode proteins which bind to Wolframin protein sequences (binding partner polypeptides). For example, a cDNA library can be produced from mRNA from a embryonic or other suitable cell type. Such a cDNA library cloned in a yeast two-hybrid expression system (Chien et al. (1991) Proc. Natl. Acad. Sci. (U.S.A.) 88: 9578) can be used to identify cDNAs which encode proteins that interact with Wolframin protein and thereby produce expression of the GALA or lexA-dependent reporter gene.

Example 1 outlined below details the methodology used to determine that carboxypeptidase E is a binding partner for Wolframin protein.

Once carboxypeptidase E was identified as a binding partner, we appreciated that cells expressing the interacting proteins in a two hybrid format can themselves form the basis of a screen The invention therefore provides hybrid screening assays and related host organisms (typically unicellular organisms) which harbor a mammalian Wolframin protein two-hybrid system, typically in the form of polynucleotides encoding a first hybrid protein, a second hybrid protein, and a reporter gene, wherein said polynucleotide(s) are either stably replicated or introduced for transient expression. In one embodiment, the host organism is a yeast cell (e.g., Saccharomyces cervisiae) in which the reporter gene transcriptional regulatory sequence comprises a Gal4-responsive promoter. This high throughput system is detailed in Example 2.

Additional methodology can be performed to eliminate the likelihood of artifacts in the screening process and is detailed below in Example 3.

Many DNA binding domains and transcriptional activating domains can be used in this invention including without limitation the DNA binding domains of GAL4, LexA, and the human estrogen receptor paired with the acidic transcriptional activating domains of GALA or the herpes virus simplex protein VP16 (See, e.g.,. Hannon et al., Genes Dev. 7, 2378, 1993; Zervos et al., Cell 72, 223, 1993; A. B. Vojtek et al., Cell 74, 205, 1993; Harper et al., Cell 75, 805, 1993; Douarin et al., Nucl. Acids Res. 23, 876, 1995). A number of plasmids known in the art can be constructed to contain the coding sequences for the fusion proteins using standard laboratory techniques for manipulating DNA. Suitable detectable reporter genes include the *E. coli* lacZ gene, whose expression may be measured colorimetrically (see, e.g., Fields and Song, supra), and yeast selectable genes such as HIS3 (Harper et al., supra; Vojtek et al., supra; Hannon et al, supra) or URA3 (Le Douarin et al., supra). Methods for transforming cells are also well known in the art. See, e.g., A. Hinnen et al., Proc. Natl. Acad. Sci. U.S.A. 75, 1929–1933, 1978. The test compound may comprise part of the cell culture medium or it may be added separately. The tester cell need not be a yeast cell, but may be a bacterial, other fungal, or mammalian cell.

A two-hybrid system useful in bacteria is based on a methodology developed by Dove et al. of Harvard Medical School (1997), Nature 386: 627–630 and Dove, S. L. and Hochschild, A., (1998) Genes & Development 12:745–754). The method can be purchased in kit form from Stratagene and is designated the "BacterioMatch™ two-hybrid system". The system is also based on transcriptional activation: A protein of interest (the bait) is fused to the full-length bacteriophage λ cI protein (λ cI), containing the amino-terminal DNA-binding domain and the carboxyl-terminal dimerization domain. The corresponding target protein is fused to the N-terminal domain of the a-subunit of RNA polymerase. The bait is tethered to the 1 operator sequence upstream of the reporter promoter through the DNA-binding domain of λ cI. When the bait and target interact, they recruit and stabilize the binding of RNA polymerase close to the promoter and activate the transcription of a reporter gene, which in our case is the $Amp^R$ gene. A second reporter gene, β-galactosidase, is expressed from the same activatable promoter, providing an additional mechanism to validate the bait and target interaction.

Mammalian two hybrid systems have been described. Representative systems are described in U.S. Pat. Nos. 6,316,223 and 6,251,676 (herein incorporated by reference). A mammalian two hybrid system can also be purchased as a kit (Stratagene's Mammalian Two-Hybrid assay kit) which is based on methodology developed by Dang et al. (1991) Mol. Cell Biol. 11:954–962. In this kit the protein of interest, or bait, is expressed as a fusion protein with the GALA DNA binding domain, and the target protein is expressed with the NF-κK activation domain. If the bait and target proteins interact, the activation domain is brought together with the DNA binding domain with subsequent transcriptional activation of the luciferase reporter gene.

It will be appreciated that in-vivo systems can be used to assess a protein-protein interaction like that between a Wolframin protein and its binding partner other than those making use of a DNA binding domain and a transcriptional activation domain. By way of non-limiting example U.S. Pat. No. 5,776,689 (herein incorporated by reference) entitled "Protein Recruitment System" describes a system wherein Protein-protein interactions in the cytoplasm are detected by recruitment of the human Sos gene product (hSos) to the membrane of the cell where it activates the Ras pathway. A commercial system, the "CytoTrap™ system" (Stratagene), uses a unique yeast strain which contains a temperature-sensitive mutation in the cdc25 gene, the yeast homologue for hSos. This protein, a guanyl nucleotide exchange factor, is essential for activation of the Ras pathway and ultimately for the survival and growth of the cell. The mutation in the cdc25 protein is temperature sensitive; the cells can grow at 25° C. but not at 37° C. This cdc25 mutation can be complemented by the hSos gene product to allow growth at 37°, providing that the hSos protein is localized to the membrane via a protein-protein interaction.

Example 1, 2 and 3 discussed above are presented below.

EXAMPLE 1

Vector Construction

The DNA encoding amino acids 1 through 306 of human Wolframin fragment was amplified by PCR from the human WFS 1 DNA sequence using primers designed to create an EcoR1 site on the 5' end of the sequence and a Not1 site on the 3' end of the sequence. The forward primer used was 5'GATCGAATTCATGGACTCCAACAC-TGCTC3' corresponding to bases 1 through 19 of the WFS1 sequence, and the reverse primer used was 5'GATCGCGGCCGCCATGT-CAATCAGGTACTC3' corresponding to bases 900 through 918 of the WFS1 sequence. Primers were synthesized by Sigma/Genosys Corp., The Woodlands, Tex. PCR reactions were assembled using the components of the Expand Hi-Fi PCR System™ (Roche Molecular Biochemicals, Indianapolis, Ind.). The following cycling program was executed: Pre-soak at (94° for 3 min.) followed by 25 cycles of [(94° for 45 sec.) then (55° C. for 1 min.) then (72° for 45 sec.)]. The resulting 918 bp PCR product was purified using a Qiagen rapid spin column (Qiagen Inc., Valencia, Calif.), and digested with the restriction enzymes EcoR1 and Not1 (New England Biolabs, Beverly, Mass.). The digested PCR product was then ligated into the yeast two hybrid expression vector pLexA (Clonetech Labs, Palo Alto, Calif.) to create an in-frame fusion with the DNA binding domain encoded by the plasmid. The accuracy of the resulting construct, pLexA-WFS, was confirmed by DNA sequence analysis.

Yeast Two Hybrid Screening

The yeast host strain EGY48 was transformed with the β-galactosidase reporter plasmid p8op-lacZ and pLexA-WFS. Yeast carrying both plasmids were selected by growth on yeast minimal medium lacking the nutrients uracil and histidine. The resulting yeast strain, EGY48[(p8op-lacZ)(pLexA-WFS)] was then transformed with a human brain cDNA library constructed in the yeast two hybrid vector pB42AD (Clonetech Labs, Palo Alto, Calif.). Transformants were selected on yeast minimal media lacking the nutrients uracil, histadine and tryptophan. Interactions between the WFS fusion protein and clones represented in the human brain library were detected by selection on yeast minimal medium lacking glucose, but containing galactose and rafinose as a carbon source, the β-galactosidase indicator X-gal, and lacking the nutrients uracil, histadine, tryptophan and leucine. A positive interaction is indicated by the growth of the colony in medium lacking leucine, and a blue color reaction. Leucine$^+$, blue colonies were selected. Plasmids were recovered by selected colonies using the Zymoprep kit from Zymo Research, Orange, Calif. The library plasmid encoding fusion protein in the vector pB42AD was transformed to the *E.coli* host strain KC8 and selection on medium lacking tryptophan. The DNA sequence of the fusion protein was determined.

Results

One of the plasmids identified from this screen as encoding a protein which would interact with the N-terminal 306 amino acids of Wolframin protein was found to encode a portion of the peptidase carboxypeptidase-E. The clone consisted of the carboxypeptidase-E sequence between base pairs 232 and 840 (amino acids to 78 to 280). Additional experimentation has shown that putting a stop codon at position 136 (a clone containing only the first 135 amino terminal amino acids of Wolframin protein) is sufficient to mediate an interaction with the same carboxypeptidase E binding partner polypeptide. It is to be appreciated that even shorter fragments (and obviously longer ones as well) likely are capable of mediating this interaction.

Carboxypeptidase-E (also known as carboxypeptidase-H or enkephalin convertase) is an exopeptidase that cleaves neuropeptides with C-terminal basic amino acids, producing an active form of the peptide. It also functions as a sorting receptor for hormones and neuropeptides in the regulated secretory pathway. Mutations in Wolframin may affect its interaction with carboxypeptidase E. This could subsequently affect carboxypeptidase E function in the sorting and processing of secreted proteins (including vasopressin, POMC, BDNF and insulin).

EXAMPLE 2

High Throughput Assay Based on the Two-hybrid System for Identifying Compounds which Modulate the Interaction of Wolframin Protein and Carboxypeptidase E or Carboxypeptidase E Fragments To develop a high throughput screen based on the two-hybrid system, a procedure is devised similar to that described in U.S. Pat. No. 6,127,521 to quantitate protein-protein interaction mediated by a small molecule. Since protein-protein interaction in the two-hybrid system stimulates transcription of the lacZ reporter gene, the assay utilizes a substrate of beta-galactosidase (the lacZ gene product lacZ gene product) which when cleaved produces a chemiluminescent signal that can be quantitated. This assay can be performed in microtiter plates, allowing thousands of compounds to be screened per week.

The assay includes the following steps:

1. Innoculate yeast cells transformed with plasmids encoding the binding domain:wolframin fusion protein, the activation domain:carboxypeptidase-e fusion protein, and the lacZ reporter gene to 50 ml of synthetic growth medium containing galactose as a carbon source and lacking uracil, histadine and tryptophan. Incubate the flask overnight at 30° C. with shaking @200 rpm.
2. Dilute the overnight culture into 1 liter of growth medium (described above) to a final A600 of 0.02 and incubate the flask overnight at 30° C. with shaking @200 rpm.
3. Dilute the second overnight culture to a final A600 of 0.5 in growth medium. Using a Quadra 96 pipettor (TomTec, Inc.), dispense 135 mu l aliquots of the cell suspension into wells of a round bottom microtiter plate pre-loaded with 15 μl/well of the compound to be tested at various concentrations. (The compounds are dissolved in 5% dimethyl sulfoxide, so that the final DMSO concentration added to cells is 0.5% which does not perturb yeast cell growth.) Cover microtiter plates and incubate at 30° C. for 4 hr with shaking at 300 rpm.
4. Centrifuge microtiter plate for 10 min at 2000 rpm. Remove the supernatant with the Quadra 96 pipettor and wash with 225 μl phosphate buffered saline.
5. Dispense 100 μl of lysis buffer (100 mM2HPO4 pH 7.8; 0.2% Triton X-100; 1.0 mM ditiothriotol) into each well, cover, and incubate for 30 min at room temperature with shaking at 300 rpm.
6. Dispense into each well of a Microfluor plate (Dynatech Laboratories, Chantilly, Va.), 50 μl of the chemiluminescent substrate, Galacton Plus TM (Tropix, Inc., Bedford, Mass.) in diluent (100 mM Na2HPO4, 1 mM MgCl2, pH 8.0).

To these wells, transfer 20 µl of cell lysate and incubate in the dark for 60 min at room temperature.

7. Add to each well 75 µl of Emeral TM accelerator. Cover plate and count in a Topcount scintillation counter (Packard, Inc.) for 0.01 min/well.

Such an assay can yield different classes of modulator compounds including (i) agonist compounds, those that enhance the interaction between a Wolframin protein and carboxypeptidase E, (ii) antagonist compounds, or those that diminish the strength of the interaction between Wolframin protein and carboxypeptidase E.

The protein interactions mediated by the test compounds and measured in this assay can be correlated with antidepressant activity in animal models well known in the art or confirmed by biochemical assays to directly assess the interaction of Woframin protein and carboxypeptidase E.

Using the quantitative chemiluminescence assay described above, the interaction of Wolframin protein and carboxypeptidase E can be analyzed in the presence and absence of potential modulator compounds. Interaction between Wolframin protein and carboxypeptidase E can be measured as a function of drug concentration.

Ideally the basal levels of beta-galactosidase in the negative controls are 0.1 per cent or less of the maximum levels detected in the yeast strain containing the Wolframin protein and carboxypeptidase E constructs.

A decrease in the level of beta-galactosidase in the cell in the presence of a compound relative to a parallel sample incubated in the absence of compound indicates the compound is an antagonist. An increase in the level beta-galactosidase in the cell in the presence of a compound relative to a parallel sample incubated in the absence of compound indicates the compound is an agonist.

EXAMPLE 3

In order to identify negative modulators of the interaction between Woframin protein and carboxypeptidase E the counterselection/ cycloheximide sensitivity method of Young et al. can be utilized. Young, K et al. Nature Biotechnology 16 946–950 (1998). This method has the advantage of eliminating artifactual elimination of compounds which demonstrate some toxicity at high doses, but desireable effects at lower concentrations.

In this method the negative selection marker CHY2 is cloned such that its expression is controlled by the LexA operator. Expression of this reporter gene confers toxicity in particular yeast backgrounds when the cells are incubated on cyclohexamide plates. When this yeast strain also expresses wolframin in the pLexA vector and the carboxypeptidase e in the pB42AD vector, the interaction of wolframin and carboxypeptidase E will result in the expression of the CHY2 gene resulting inhibition of cell growth in the presence of cyclohexamide. These yeast are plated on agar media containing cyclohexamide and compounds to be screened spotted on the plates. Any compound which disrupts the wolframin:carboxypeptidase E interaction will result in inhibition of CHY2 expression and allow cell growth. This agar diffusion format provides an inherent compound titration gradient upon a single point compound application. Thus compounds which demonstrate some toxicity at high doses, but desireable effects at lower concentrations are not discarded as false negatives.

In-Vitro Assays of the Invention

In designing assays to assess the association of Wolframin protein with carboxypeptidase E it is often desirable to obtain isolated preparations of both polypeptides. Obtaining isolated samples of Wolframin and Carboxypeptidase E are both easily accomplished by the ordinarily skilled artisan.

Isolated Wolframin protein can be obtained in several different ways; by purification from membrane extracts from normal cells or tissues, or from cells that have been genetically engineered to overexpress Wolframin protein by conventional purification procedures. Alternatively, fragments of Wolframin protein can be recombinantly expressed and purified. Generally it is anticipated that the Wolframin protein will be found primarily embedded in the membranes fraction of cells which express it. However it is appreciated that DNA constructs which encode Wolframin protein fragments lacking transmembrane domains would likely find their way to the cytosol. Wolframin protein can be isolated by way of non-limiting example by any of the methods below.

Separation of Wolframin protein and succeeding purification may be conducted utilizing means which have been commonly used for the purification of membrane proteins. For example, a method wherein a cell membranes are solubilized using detergents followed by purification with various chromatographic means is a known technique which may be employed in the present invention.

Purification of Wolframin polypeptide or Wolframin protein fragments can be accomplished using a variety of techniques. If the polypeptide has been synthesized such that it contains a tag such as Hexahistidine (Wolframin protein/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing wolframin protein). For example, polyhistidine binds with great affinity and specificity to nickel, thus an affinity column of nickel (such as the Qiagen Registered TM nickel columns) can be used for purification of Wolframin/polyHis. (See for example, Ausubel et al., eds., Current Protocols in Molecular Biology, Section 10.11.8, John Wiley & Sons, New York [1993]).

Even if the Wolframin protein is prepared without a label or tag to facilitate purification. The Wolframin protein or Wolframin protein fragments of the invention may be purified by immunoaffinity chromatography. To accomplish this, antibodies specific for the Wolframin protein must be prepared by means well known in the art. Antibodies generated against the Wolframin protein are prepared by administering the polypeptides or epitope-bearing fragments, analogues or cells to an animal, preferably a nonhuman, using routine protocols. By way of example, both the N-terminal (aa2-242) and C-terminal hydrophilic (aa 651-864) domains of Wolframin protein and been cloned and expressed in E.coli as 6X-His fusion proteins. These fusion proteins have been purified and used to produce rabbit antisera to Wolframin protein. Western blotting demonstrated that these antisera recognize Wolframin protein when overexpressed in tissue culture, and could also be used to immuneprecipitate a protein of the expected molecular weight from rat hippocampus. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al., Immunology Today 4: 72 (1983); Cole et al., pg. 77–96 in Monoclonal Antibodies and Cancer Therapy, Alan R. Liss, Inc. (1985).

Where the Wolframin protein or Wolframn protein fragment is prepared without a tag attached, and no antibodies are available, other well known procedures for purification can be used. Such procedures include, without limitation, ion exchange chromatography, affinity chromatography, molecular sieve chromatography, HPLC, native gel electrophoresis in combination with gel elution, and preparative isoelectric focusing ("Isoprime"machine/technique, Hoefer Scientific). In some cases, two or more of these techniques may be combined to achieve increased purity.

Isolated Carboxypeptidase E binding partner polypeptides or can be obtained in several different ways; by purification from membrane extracts or culture media from normal cells or tissues, or from cells that have been genetically engineered to overexpress Carboxypeptidase E binding partner polypeptides by conventional purification procedures. Alternatively, Carboxypeptidase E binding partner polypeptides can be recombinantly expressed and purified. The discussion above with regard to the isolation of Wolframin protein that has been tagged or by immunoaffinity is applicable to the isolation of Carboxypeptidase E binding partner polypeptides as well.

Carboxypeptidase E has been purified to apparent homogeneity in at least one published procedure. (Fricker et al. J Biol. Chem. 258:10950 (1983)). Soluble and membrane associated forms have similar enzymatic and physical properties (Fricker, J. Cell. Biochem., supra). The published procedure relies on successive chromatography steps over DEAE cellulose, ConA Sepharose and a Sepharose-6B p-aminobenzoyl-L-arginine affinity column. Column fractions were assayed using an assay which utilizes a solubility change incurred when a water soluble substrate is converted to a chloroform soluble product. In a typical assay, 25 µl of the fraction is combined with 225 µl of 0.1M NaAc pH5.5, 0.01% Triton X-100, and 0.2mM dansyl-Phe-Ala-Arg. After incubation at 37° C. for 1 hour, the reaction was terminated by acidification with 10 µl of 1N HCl. Reaction products are quantitated by measuring fluorescence (360 nm excitation, 510 nm emission wavelength) following extraction into chloroform (Fricker, L D. (1995) *Methods Neurosci.* 23, 237–250).

EXAMPLE 4

Purification of a Wolframin Protein Fragment

The amino terminal 242 amino acid polypeptide of the human WFS1 protein was cloned in the pProEX HT vector (Life Technologies, Rockville, Md.) and transfected into *E.coli* strain BL21. Three liters of prewarmed LB medium containing 100 µg/ml ampicillin was inoculated with 300 ml of an overnight culture. The culture was grown at 37° C. while shaking at 250 rpm, until the $Abs_{600\ nm}$ reached 0.6. Expression was induced by addition of IPTG to a final concentration of 0.6 mM. The cultures were grown for an additional three hours at 37° C. while shaking at 250 rpm. Cells were harvested by centrifugation at 6,000×g for 15 minutes at 4° C. Cells were resuspended in lysis buffer (50 mM $NaH_2PO_4$, 300 mM NaCl, 10 mM imidazole, pH 8.0) to a final volume of 35 ml. Cells were lysed at 15,000 psi using a French Pressure Cell Press (Spectronic Instruments, Rochester, N.Y.). Cell debris was removed by centrifugation at 100,000×g for 60 minutes at 4° C. in a model L8-M ultracentrifuge and a SW-28 rotor (Beckman Instruments, Palo Alto, Calif.). The cleared supernatant was incubated with 5 ml of a nickel-nitrilotriacetic acid (Ni-NTA) agarose overnight at 4° C. with gentle mixing. The slurry was loaded into a column and the packed Ni-NTA agarose was washed with 100 ml of wash buffer (50 mM $NaH_2PO_4$, 300 mM NaCl, 20 mM imidazole, pH 8.0). The column was then washed sequentially with 20 ml of wash buffer containing 50 mM, 100 mM and 250 mM imidazole. Bound polypeptide was eluted with 20 ml of was buffer containing 500 mM imidazole. The eluted polypeptide was dialyzed extensively in Dulbecco's phosphate buffered saline (PBS, Life Technologies, Gaithersburg, Md.) and then concentrated 10-fold. Typical yield was 1 mg of polypeptide per one liter of culture. It will be appreciated that a similar protocol could be designed to produce a Wolframin protein fragment polypeptide of virtually any length which is capable of stable expression within the expressing cell.

Design of In-Vitro Assays

An in vitro assay is then designed that would detect the binding between the full length Wolframin protein polypeptide or a Wolframin protein fragment and a carboxypeptidase E binding partner polypeptide. For this purpose an easy detection system should be available for at least one of the partners in the complex; such a detection system could be based on antibodies, or on labeling one of the proteins with a marker molecule or radioactivity. The subsequent use of this assay would be to screen a compound collection for substances that would modulate the interaction between a carboxypeptidase E binding partner polypeptide and Wolframin protein.

In solution assays, methods of the invention comprise the steps of (a) contacting a Wolframin protein polypeptide with one or more candidate inhibitor compounds and (b) identifying the compounds that modulate the Wolframin protein polypeptide association with a carboxypeptidase E binding partner polypeptide Agents that modulate (i.e., increase, decrease) Wolframin protein polypeptide association with other proteins or expression may be identified by incubating a putative modulator with a cell expressing a Wolframin protein polypeptide and determining the effect of the putative modulator on Wolframin protein activity or expression. Modulators of Wolframin protein activity will be therapeutically useful in treatment of diseases and physiological conditions in which normal or aberrant Wolframin protein activity is involved.

Binding assays often take one of two forms: immobilized Wolframin protein polypeptide(s) can be used to bind labeled binding partner polypeptide(s), or conversely, immobilized binding partner polypeptide(s) can be used to bind labeled Wolframin protein polypeptides. In each case, the labeled polypeptide is contacted with the immobilized polypeptide under conditions that permit specific binding of the polypeptides(s) to form a complex in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. Additions, deletions, modifications (such as pH) and substitutions (such as KCl substituting for NaCl or buffer substitution) may be made to these basic conditions. Modifications can be made to the basic binding reaction conditions so long as specific binding of Wolframin protein polypeptide(s) to carboxypeptidase E binding partner polypeptide occurs in the control reaction(s). In such reactions, at least one polypeptide species typically is labeled with a detectable marker. Suitable labeling includes, but is not limited to, radiolabeling by incorporation of a radiolabeled amino acid (e.g., $^{14}$C-labeled leucine, $^3$H-labeled glycine, $^{35}$S-labeled methionine), radiolabeling by post-translational radioiodination with $^{125}$I or $^{131}$I (e.g., Bolton-Hunter reaction and chloramine T), labeling by post-translational phosphorylation with $^{32}$P (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments a Wolframin protein or a carboxypeptidase E binding partner polypeptide may be used in combination with an accessory protein (e.g., a protein which forms a complex with the polypeptide in vivo). It is typically preferred that different labels are used for each polypeptide species, so that binding of individual and/or heterodimeric and/or multimeric complexes can be readily distinguished. For example but not by way of limitation, a Wolframin protein polypeptide is labeled with fluorescein and an accessory polypeptide is labeled with a fluorescent marker that fluoresces with either a different excitation wavelength or emission wavelength, or both. Alternatively, double-label scintillation counting is used, wherein a Wolframin protein polypeptide is labeled with one isotope (e.g., $^3$H) and a binding partner polypeptide species is labeled with a different isotope (e.g., $^{14}$C) that can be distinguished by scintillation counting using standard discrimination techniques.

Labeled polypeptide(s) are contacted with immobilized polypeptide(s) under aqueous conditions as described herein. The time and temperature of incubation of a binding reaction is optionally varied, with the selected conditions permitting specific binding to occur in a control reaction where no agent is present. Preferable embodiments employ a reaction temperature of about at least 15 degrees Centigrade, more preferably 30 to 42 degrees Centigrade, and a time of incubation of approximately at least 15 seconds, although longer incubation periods, from 30 seconds to a minute to several minutes or more, are preferable so that, in some embodiments, a binding equilibrium is attained. Binding kinetics and the thermodynamic stability of bound Wolframin protein:binding partner complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other standard analytic methods (Proteins, Structures and Molecular Principles, (1984) Creighton (ed.), W. H. Freeman and Company, New York).

Specific binding of labeled Wolframin protein or a carboxypeptidase E binding partner polypeptide to immobilized Wolframin protein or a carboxypeptidase E binding partner polypeptide polypeptide, respectively, is determined by including unlabeled competitor protein(s) (e.g., albumin). Similarly, specific binding of labeled Wolframin protein or binding partner polypeptide to immobilized binding partner or Wolframin protein polypeptide, respectively, is determined by including unlabeled competitor protein(s) (e.g., albumin). After a binding reaction is completed, labeled polypeptide(s) specifically bound to immobilized polypeptide is detected. For example and not by way of limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding between a Wolframin protein polypeptide and a binding partner polypeptide in a control binding reaction. Blocking agents are included to inhibit nonspecific binding of labeled protein to immobilized protein and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tjian (1986) Proc. Natl. Acad. Sci. (U.S.A.) 83: 5889). One example, not for limitation, is covalent linkage to a substrate derivatized with cyanogen bromide (such as CNBr-derivatized Sepharose 4B). It may be desirable to use a spacer to reduce potential steric hindrance from the substrate. Noncovalent bonding of proteins to a substrate include, but are not limited to, bonding of the protein to a charged surface (e.g., on a bead) and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a Wolframin protein polypeptide to a binding partner polypeptide or disrupt, modulate, inhibit, or potentiate the activity of either or both. Agents which, when added to a binding reaction, inhibit formation of Wolframin protein:binding partner complexes are thereby identified as Wolframin protein inhibitors; Agents which, when added to a binding reaction, enhance formation of Wolframin protein:binding partner complexes are thereby identified as Wolframin protein potentiators (e.g., Wolframin protein agonists;).

In a preferred embodiment, several binding reactions are monitored simultaneously, e.g., using a format which permits simultaneous analysis of several samples (microtiter plates, etc.). In a preferred embodiment, the assays are automated, e.g., using robotics for pipetting samples into microtiter plates.

One means for detecting binding of a Wolframin protein polypeptide to a binding partner polypeptide is to immobilize the Wolframin protein polypeptide, such as by covalent or noncovalent chemical linkage to a solid support, and to contact the immobilized Wolframin protein polypeptide with a binding partner polypeptide that has been labeled with a detectable marker (e.g., by incorporation of radiolabeled amino acid, by epitope tagging and reporting with a fluorescent-labelled anti-epitope tag antibody, and the like). Such contacting is typically performed in aqueous conditions which permit binding of a Wolframin protein polypeptide to a binding partner polypeptide. Binding of the labeled binding partner polypeptide to the immobilized Wolframin protein is measured by determining the extent to which the labeled binding partner polypeptide is immobilized as a result of a specific binding interaction. Such specific binding may be reversible, or may be optionally irreversible if a cross-linking agent is added in appropriate experimental conditions. Agents that inhibit or augment the formation of bound complexes as compared to a control binding reaction lacking agent are thereby identified as Wolframin protein-modulating agents and are candidate therapeutic agents.

Binding assays often take one of two forms: immobilized Wolframin protein polypeptide(s) can be used to bind labeled binding partner polypeptide(s), or conversely, immobilized binding partner polypeptide(s) can be used to bind labeled Wolframin protein polypeptides. In each case, the labeled polypeptide is contacted with the immobilized polypeptide under conditions that permit specific binding of the polypeptides(s) to form a complex in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. Additions, deletions, modifications (such as pH) and substitutions (such as KCl substituting for NaCl or buffer substitution) may be made to these basic conditions. Modifications can be made to the basic binding reaction conditions so long as specific binding of Wolframin protein polypeptide(s) to binding partner polypeptides occurs in the control reaction(s). In such reactions, at least one polypeptide species typically is labeled with a detectable marker. Suitable labeling includes, but is not limited to, radiolabeling by incorporation of a radiolabeled amino acid (e.g., $^{14}C$-labeled leucine, $^{3}H$-labeled glycine, $^{35}S$-labeled methionine), radiolabeling by post-translational radioiodination with $^{125}I$ or $^{131}I$ (e.g., Bolton-Hunter reaction and chloramine T), labeling by post-translational phosphorylation with $^{32}P$ (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker. Additionally, in some embodiments a Wolframin protein or binding partner polypeptide may be used in combination with an accessory protein (e.g., a protein which forms a complex with the polypeptide in vivo). It is typically preferred that different labels are used for each polypeptide species, so that binding of individual and/or heterodimeric and/or multimeric complexes can be readily distinguished. For example but not by way of limitation, a Wolframin protein polypeptide is labeled with fluorescein and an accessory polypeptide is labeled with a fluorescent marker that fluoresces with either a different excitation wavelength or emission wavelength, or both. Alternatively, double-label scintillation counting is used, wherein a Wolframin protein polypeptide is labeled with one isotope (e.g., $^{3}H$) and a binding partner polypeptide species is labeled with a different isotope (e.g., $^{14}C$) that can be distinguished by scintillation counting using standard discrimination techniques.

Labeled polypeptide(s) are contacted with immobilized polypeptide(s) under aqueous conditions as described herein. The time and temperature of incubation of a binding reaction is optionally varied, with the selected conditions permitting specific binding to occur in a control reaction where no agent is present. Preferable embodiments employ a reaction temperature of about at least 15 degrees Centigrade, more preferably 30 to 42 degrees Centigrade, and a time of incubation of approximately at least 15 seconds, although longer incubation periods, from 30 seconds to a minute to several minutes or more, are preferable so that, in some embodiments, a binding equilibrium is attained. Binding kinetics and the thermodynamic stability of bound Wolframin protein:binding partner complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other standard analytic methods (Proteins, Structures and Molecular Principles, (1984) Creighton (ed.), W. H. Freeman and Company, New York).

Specific binding of labeled Wolframin protein or binding partner polypeptide to immobilized Wolframin protein or binding partner polypeptide, respectively, is determined by including unlabeled competitor protein(s) (e.g., albumin). Similarly, specific binding of labeled Wolframin protein or binding partner polypeptide to immobilized binding partner or Wolframin protein polypeptide, respectively, is determined by including unlabeled competitor protein(s) (e.g., albumin). After a binding reaction is completed, labeled polypeptide(s) specifically bound to immobilized polypeptide is detected. For example and not by way of limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding between a Wolframin protein polypeptide and a binding partner polypeptide in a control binding reaction. Blocking agents are included to inhibit nonspecific binding of labeled protein to immobilized protein and/or to inhibit nonspecific binding of labeled polypeptide to the immobilization substrate.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a Wolframin protein polypeptide to a carboxypeptidase E binding partner polypeptide or disrupt, modulate, inhibit, or potentiate the activity of either or both. Agents which, when added to a binding reaction, inhibit formation of Wolframin protein:binding partner complexes are thereby identified as Wolframin protein inhibitors; Agents which, when added to a binding reaction, enhance formation of Wolframin protein:binding partner complexes are thereby identified as Wolframin protein potentiators (e.g., Wolframin protein agonists;)

In a preferred embodiment, several binding reactions are monitored simultaneously, e.g., using a format which permits simultaneous analysis of several samples (microtiter plates, etc.). In a preferred embodiment, the assays are automated, e.g., using robotics for pipetting samples into microtiter plates.

One means for detecting binding of a Wolframin protein polypeptide to a binding partner polypeptide is to immobilize the Wolframin protein polypeptide, such as by covalent or noncovalent chemical linkage to a solid support, and to contact the immobilized Wolframin protein polypeptide with a binding partner polypeptide that has been labeled with a detectable marker (e.g., by incorporation of radiolabeled amino acid, by epitope tagging and reporting with a fluorescent-labelled anti-epitope tag antibody, and the like). Such contacting is typically performed in aqueous conditions which permit binding of a Wolframin protein polypeptide to a carboxypeptidase E binding partner polypeptide. Binding of the labeled a carboxypeptidase E binding partner polypeptide polypeptide to the immobilized Wolframin protein is measured by determining the extent to which the labeled binding partner polypeptide is immobilized as a result of a specific binding interaction. Such specific binding may be reversible, or may be optionally irreversible if a cross-linking agent is added in appropriate experimental conditions. Agents that inhibit or augment the formation of bound complexes as compared to a control binding reaction lacking agent are thereby identified as Wolframin protein-modulating agents and are candidate therapeutic agents.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference.

What is claimed is:

1. A method for identifying agents that increase binding between a Wolframin protein polypeptide, comprising an amino acid sequence selected from the group consisting of SEQ ID NO:2, SEQ ID NO:8, and SEQ ID NO: 10, and a carboxypeptidase E binding partner polypeptide comprising an amino acid sequence selected from the group consisting of SEQ ID NO:4, SEQ ID NO 12, SEQ ID NO: 14, SEQ ID NO: 15, and SEQ ID NO:17 comprising:
    (a) contacting said Wolframin protein polypeptide and said carboxypeptidase E binding partner polypeptide in the presence and absence of a test agent;
    (b) determining binding between said Wolframin protein polypeptide and said binding partner polypeptide in the presence and absence of the test agent; and
    (c) comparing binding between said Wolframin protein polypeptide and said carboxypeptidase E binding partner polypeptide in the presence and absence of the test agent to determine whether binding between said Wolframin protein polypeptide and a said carboxypeptidase E binding partner polypeptide is increased in the presence of the test agent.

2. A method according to claim 1, wherein the Wolframin protein polypeptide is expressed in a cell transformed or transfected with a polynucleotide comprising a nucleotide sequence that encodes said polypeptide.

3. A method according to claim 1, wherein the carboxypeptidase E binding partner polypeptide is expressed in a cell transformed or transfected with a polynucleotide comprising a nucleotide sequence that encodes said polypeptide.

4. A method according to claim 1, wherein both the Wolframin protein polypeptide and the carboxypeptidase E binding partner polypeptide are expressed in a cell transformed or transfected with a polynucleotide comprising a nucleotide sequence that encodes said polypeptide, wherein said contacting step further comprises growing the cell in the presence of the test agent.

* * * * *